(12) United States Patent
Nobis et al.

(10) Patent No.: US 8,062,306 B2
(45) Date of Patent: Nov. 22, 2011

(54) MANUALLY ARTICULATING DEVICES

(75) Inventors: Rudolph H. Nobis, Mason, OH (US);
Anil K. Nalagatla, Mason, OH (US);
Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 394 days.

(21) Appl. No.: 11/610,803

(22) Filed: Dec. 14, 2006

(65) Prior Publication Data
US 2008/0147113 A1 Jun. 19, 2008

(51) Int. Cl.
*A61B 17/32* (2006.01)
(52) U.S. Cl. .................. 606/113; 606/174; 606/205
(58) Field of Classification Search .................. 606/170, 606/174, 205, 207, 208, 113; 600/139, 140, 600/141, 142, 146, 147, 149, 104; 227/19, 227/176.1, 175.1, 178.1, 179.1, 180.1, 181.1, 227/181.2
See application file for complete search history.

(56) References Cited

U.S. PATENT DOCUMENTS

| | | | | |
|---|---|---|---|---|
| 4,880,015 | A | * | 11/1989 | Nierman ........................ 600/564 |
| 5,209,747 | A | | 5/1993 | Knoepfler |
| 5,275,614 | A | * | 1/1994 | Haber et al. .................. 606/207 |
| 5,312,023 | A | | 5/1994 | Green et al. |
| 5,330,502 | A | | 7/1994 | Hassler et al. |
| 5,342,396 | A | | 8/1994 | Cook |
| 5,350,391 | A | | 9/1994 | Iacovelli |
| 5,360,428 | A | | 11/1994 | Hutchinson, Jr. |
| 5,374,277 | A | * | 12/1994 | Hassler .......................... 606/207 |
| 5,383,888 | A | | 1/1995 | Zvenyatsky et al. |
| 5,403,342 | A | | 4/1995 | Tovey et al. |
| 5,445,648 | A | | 8/1995 | Cook |
| 5,456,684 | A | | 10/1995 | Schmidt et al. |
| 5,514,157 | A | * | 5/1996 | Nicholas et al. ............... 606/206 |
| 5,549,637 | A | * | 8/1996 | Crainich ........................ 606/207 |
| 5,571,090 | A | | 11/1996 | Sherts |
| 5,582,617 | A | | 12/1996 | Klieman et al. |
| 5,607,450 | A | | 3/1997 | Zvenyatsky et al. |
| 5,609,601 | A | | 3/1997 | Kolesa et al. |
| 5,667,527 | A | | 9/1997 | Cook |
| 5,743,456 | A | | 4/1998 | Jones et al. |
| 5,766,205 | A | | 6/1998 | Zvenyatsky et al. |
| 5,782,859 | A | | 7/1998 | Nicholas et al. |
| 5,792,165 | A | | 8/1998 | Klieman et al. |
| 5,797,959 | A | | 8/1998 | Castro et al. |
| 5,810,876 | A | | 9/1998 | Kelleher |

(Continued)

FOREIGN PATENT DOCUMENTS
EP 0621009 4/1994
(Continued)

OTHER PUBLICATIONS

International Preliminary Report on Patentability, PCT Application No. PCT/US2007/087378, dated Jun. 16, 2009.

(Continued)

*Primary Examiner* — Anhtuan T Nguyen
*Assistant Examiner* — David Eastwood

(57) ABSTRACT

Methods and devices are provided for controlling movement of a working end of a surgical device, and in particular for performing various surgical procedures using an instrument having an end effector that can be articulated relative to an elongate shaft of the device. In certain embodiments, the end effector can also optionally rotate relative to the elongate shaft of the device, and/or the shaft can rotate relative to a handle of the device.

23 Claims, 21 Drawing Sheets

U.S. PATENT DOCUMENTS

| | | | |
|---|---|---|---|
| 5,827,323 | A | 10/1998 | Klieman et al. |
| 5,836,960 | A * | 11/1998 | Kolesa et al. .................. 606/170 |
| 6,024,708 | A | 2/2000 | Bales et al. |
| 6,027,522 | A | 2/2000 | Palmer |
| 6,264,664 | B1 | 7/2001 | Avellanet |
| 6,605,105 | B1 | 8/2003 | Cuschieri et al. |
| 6,613,068 | B2 | 9/2003 | Ouchi et al. |
| 6,663,641 | B1 | 12/2003 | Kovac et al. |
| 6,666,854 | B1 | 12/2003 | Lange et al. |
| 6,673,092 | B1 * | 1/2004 | Bacher ........................ 606/205 |
| 6,818,007 | B1 | 11/2004 | Dampney et al. |
| 7,052,489 | B2 | 5/2006 | Griego et al. |
| 7,087,071 | B2 | 8/2006 | Nicholas et al. |
| RE39,415 | E | 11/2006 | Bales et al. |
| 7,270,663 | B2 | 9/2007 | Nakao |
| 2002/0173805 | A1 | 11/2002 | Matsuno et al. |
| 2003/0109898 | A1 | 6/2003 | Schwarz et al. |
| 2003/0236549 | A1 * | 12/2003 | Bonadio et al. ............. 606/205 |
| 2004/0068291 | A1 | 4/2004 | Suzuki |
| 2004/0167545 | A1 | 8/2004 | Sadler et al. |
| 2004/0193212 | A1 * | 9/2004 | Taniguchi et al. ........... 606/205 |
| 2004/0225323 | A1 | 11/2004 | Nagase et al. |
| 2004/0243108 | A1 | 12/2004 | Suzuki |
| 2004/0260198 | A1 | 12/2004 | Rothberg et al. |
| 2004/0260337 | A1 | 12/2004 | Freed |
| 2005/0033312 | A1 | 2/2005 | Suzuki |
| 2005/0033357 | A1 | 2/2005 | Braun |
| 2005/0107809 | A1 | 5/2005 | Litscher et al. |
| 2005/0124912 | A1 | 6/2005 | Griego et al. |
| 2006/0016853 | A1 * | 1/2006 | Racenet .................... 227/176.1 |
| 2006/0020287 | A1 | 1/2006 | Lee et al. |
| 2006/0258954 | A1 | 11/2006 | Timberlake et al. |
| 2006/0259073 | A1 * | 11/2006 | Miyamoto et al. ............ 606/205 |
| 2007/0106317 | A1 * | 5/2007 | Shelton et al. ................ 606/170 |
| 2007/0203487 | A1 | 8/2007 | Sugita |
| 2007/0213754 | A1 | 9/2007 | Mikkaichi et al. |
| 2007/0260112 | A1 | 11/2007 | Rahmani |

FOREIGN PATENT DOCUMENTS

| | | |
|---|---|---|
| WO | 97/12557 A | 4/2007 |
| WO | 2007109171 A2 | 9/2007 |

OTHER PUBLICATIONS

International Search Report, PCT Application No. PCT/US2007/087378, dated Jul. 31, 2008.

* cited by examiner

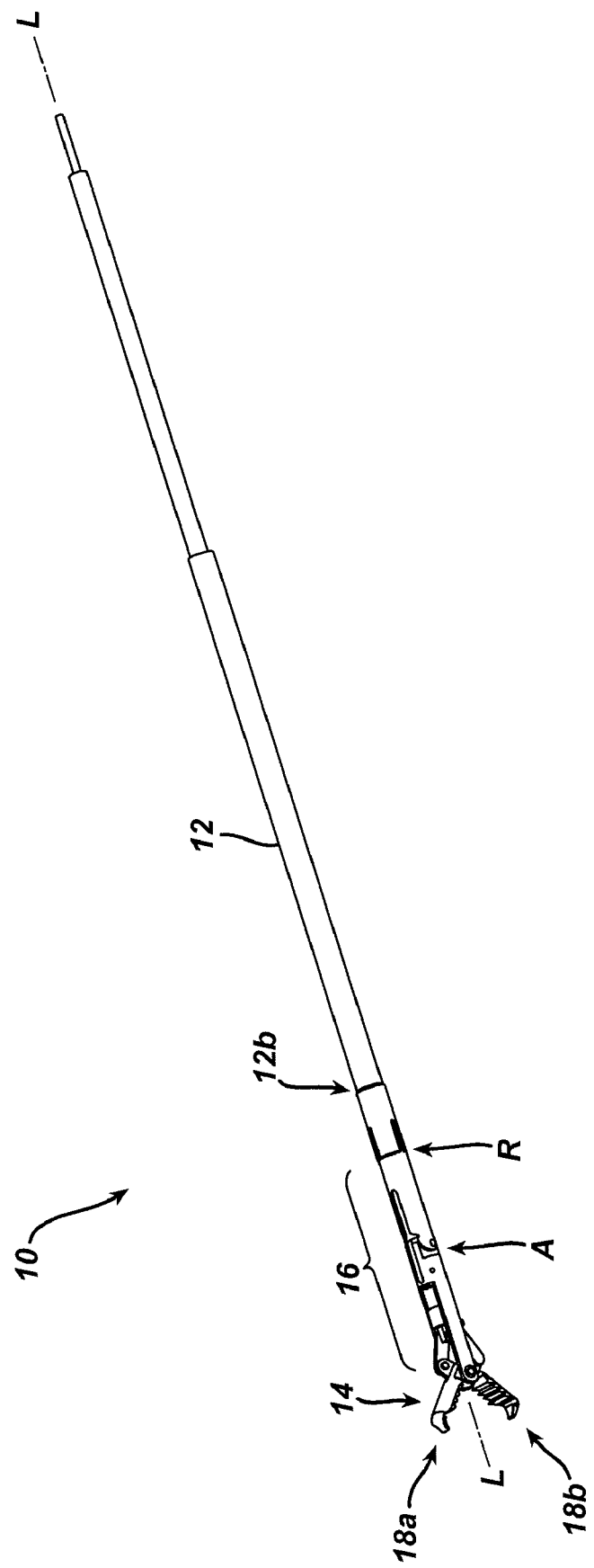

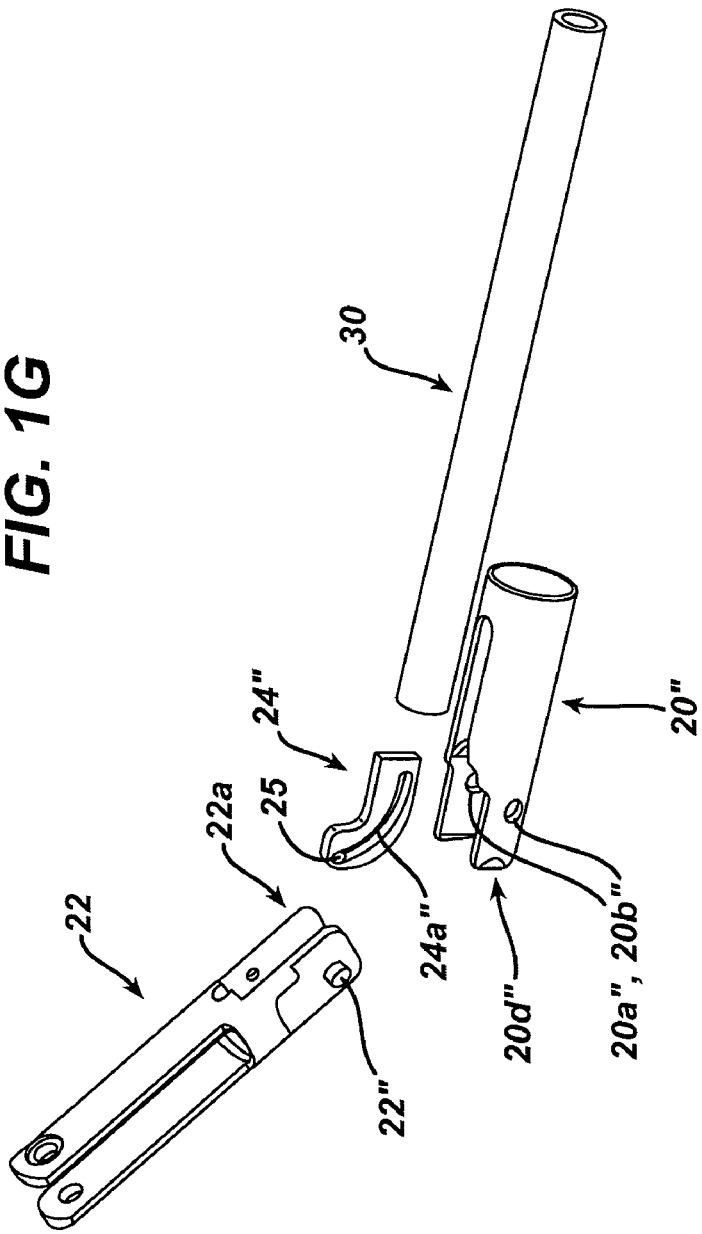

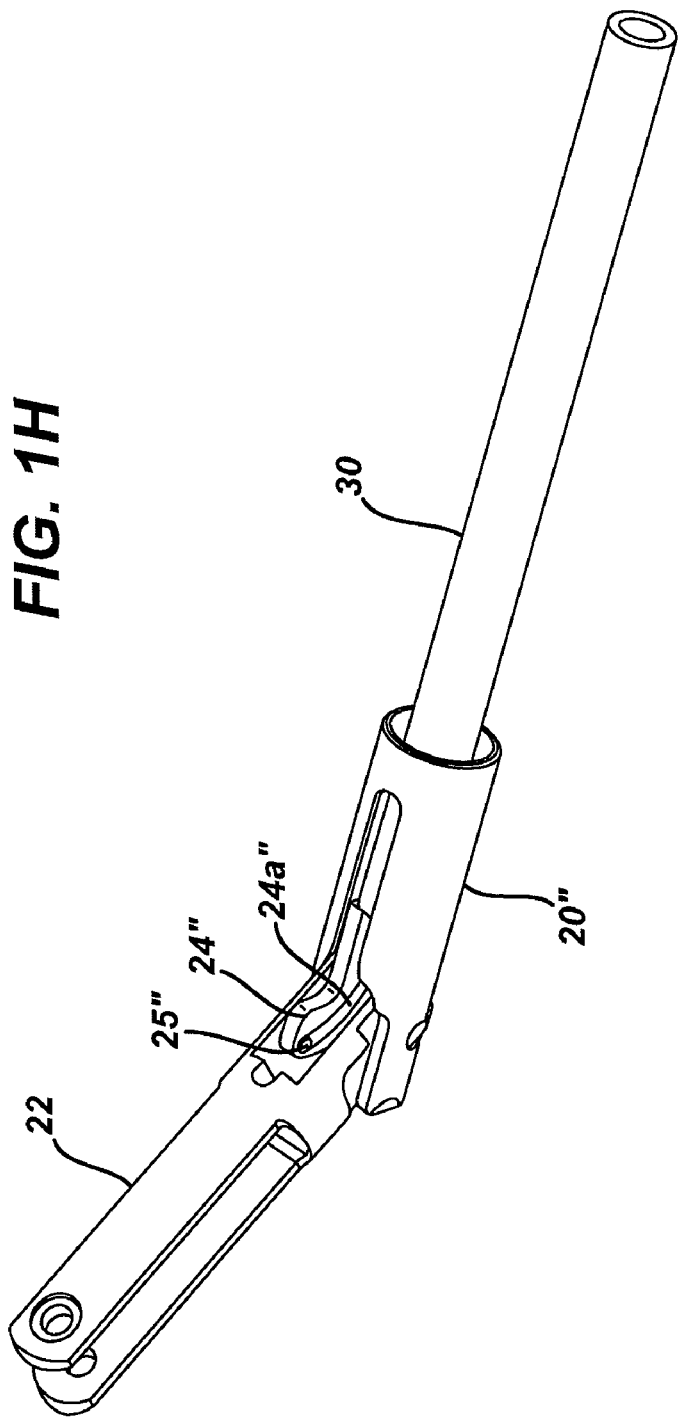

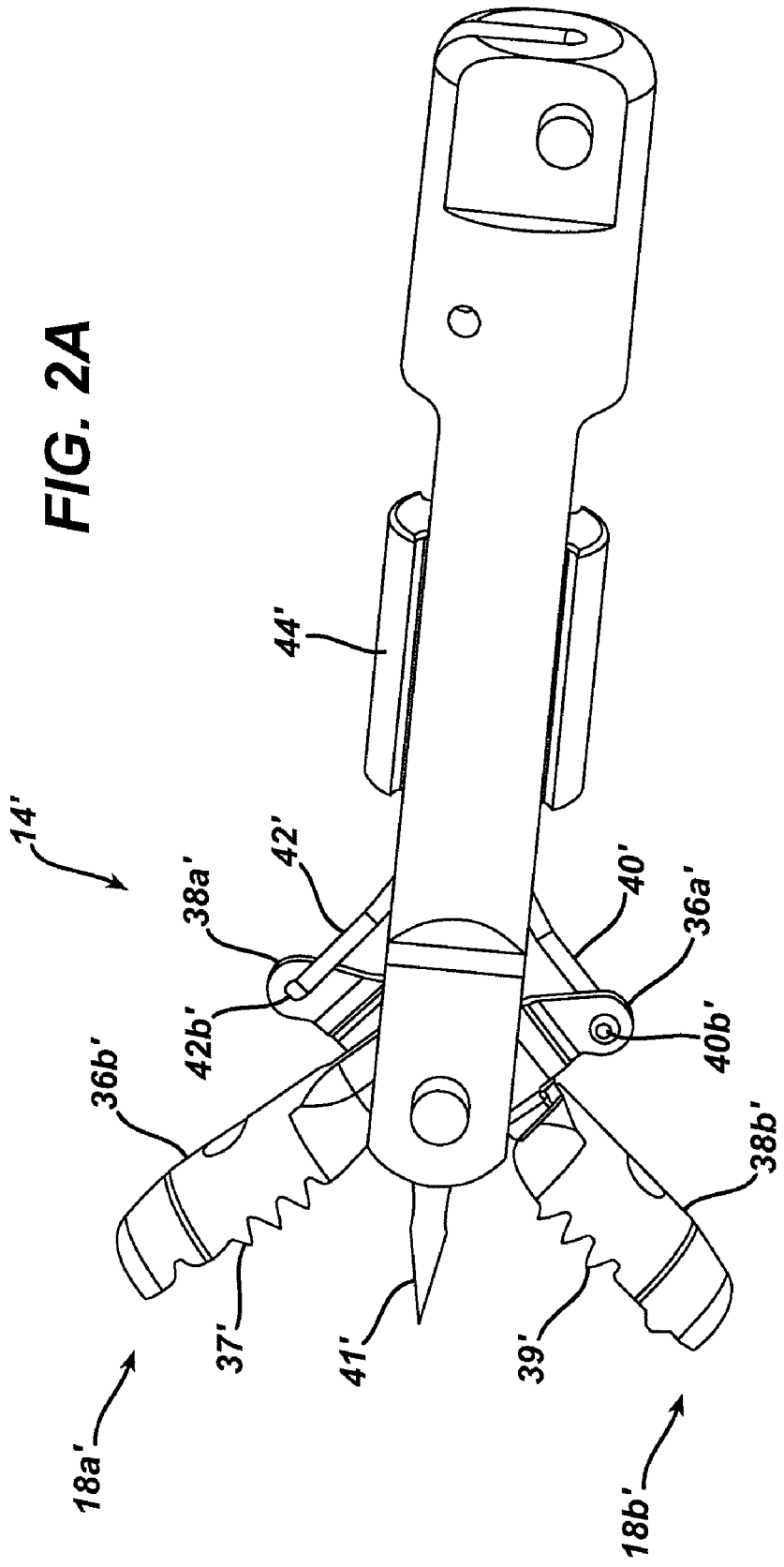

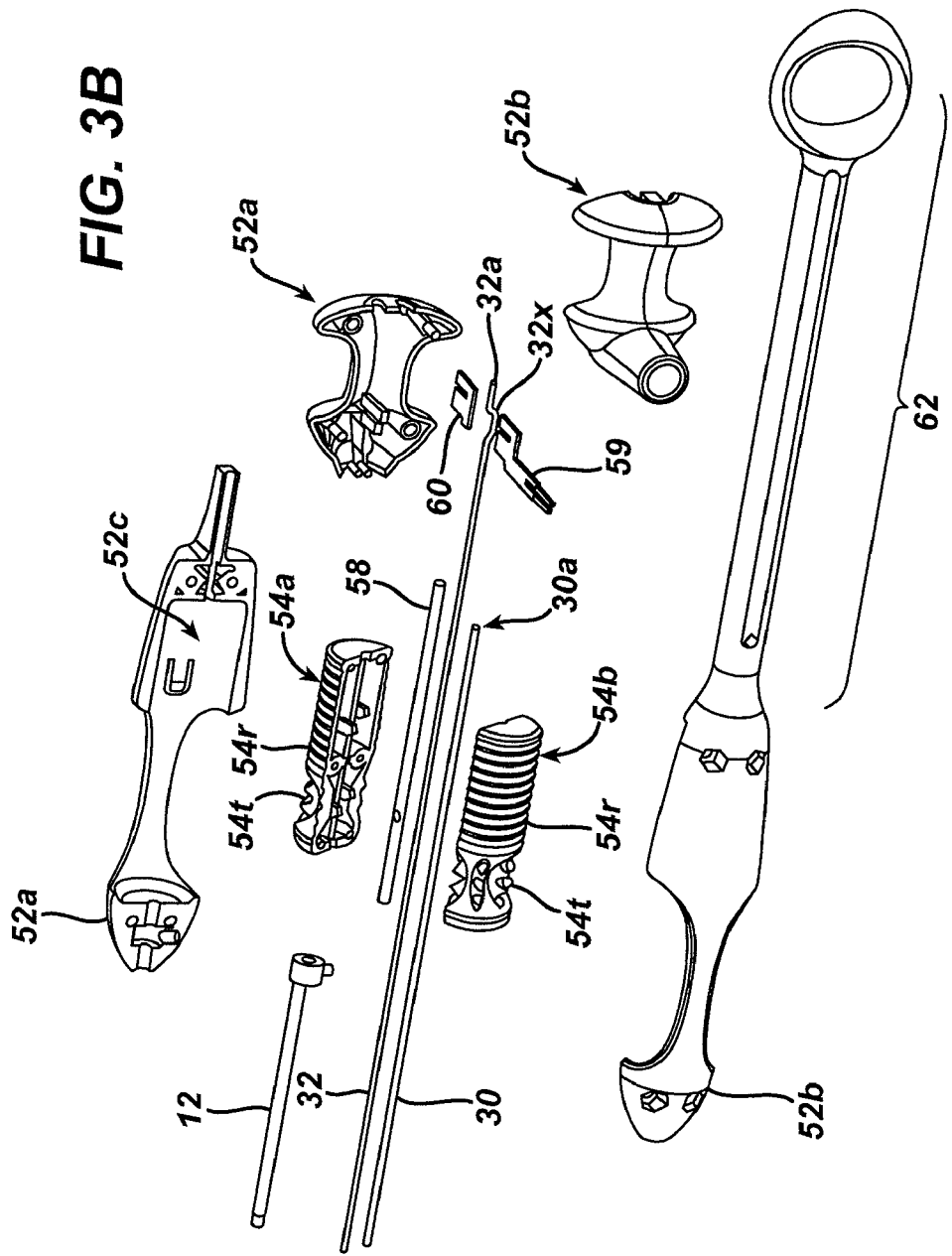

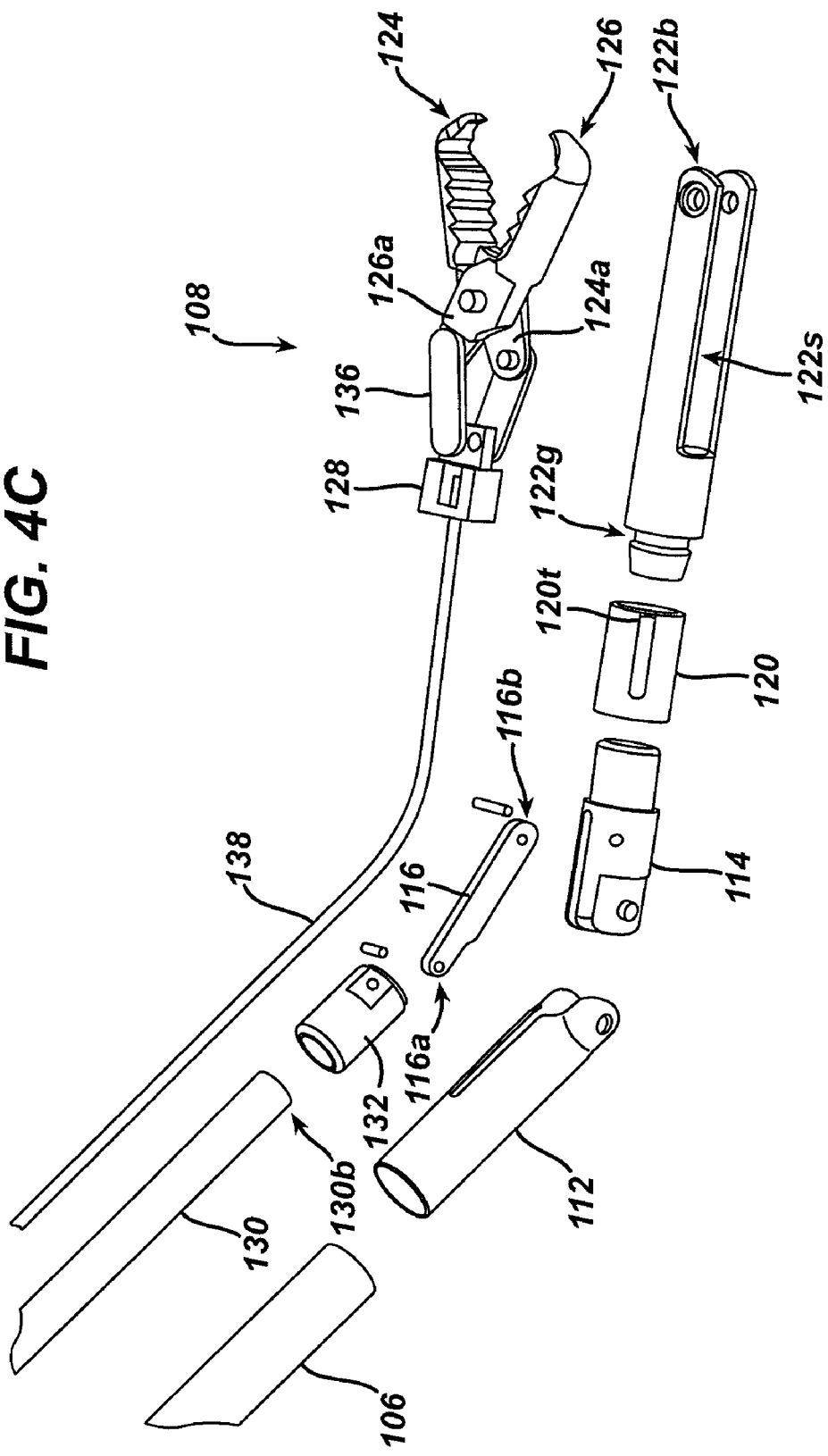

MANUALLY ARTICULATING DEVICES

FIELD OF THE INVENTION

The present invention relates methods and devices for controlling movement of a working end of a surgical device.

BACKGROUND OF THE INVENTION

In laparoscopic surgical procedures, a small incision is made in the body and an elongate shaft of a surgical device is inserted through the incision to position a distal end of the shaft at a surgical site. In endoscopic procedures, the elongate shaft of a surgical device is inserted through a natural orifice, such as the mouth or anus, and is advanced along a pathway to position a distal end of the device at a surgical site. Endoscopic procedures typically require the use of a flexible shaft to accommodate the tortuous pathway of the body lumen, whereas rigid shafts can be used in laparoscopic procedures. These tools can be used to engage and/or treat tissue in a number of ways to achieve a diagnostic or therapeutic effect.

Many current laparoscopic and endoscopic devices utilize articulating effectors to provide the user with more control over the orientation of the working end of the instrument. Integration of the controls for articulating, as well as actuating, a working end of a laparoscopic or endoscopic device tend to be complicated by the size constraints of the relatively small pathway through which it is inserted. The controls for an endoscopic device are further complicated by the flexibility of the shaft. Generally, the control motions are all transferred through the shaft as longitudinal translations, which can interfere with the flexibility of the shaft. There is also a desire to lower the force necessary to articulate and/or actuate the working end to a level that all or a great majority of surgeons can handle. One known solution to lower the force-to-fire is to use electrical motors. However, surgeons typically prefer to experience feedback from the working end to assure proper operation of the end effector. The user-feedback effects are not suitably realizable in present motor-driven devices.

Accordingly, there remains a need for improved methods and devices for controlling movement of a working end of a surgical device.

SUMMARY OF THE INVENTION

Methods and devices are provided for controlling movement of a working end of a surgical device. In one embodiment, a surgical device is provided having an elongate shaft with proximal and distal ends. A proximal end of a three-bar linkage is coupled to the distal end of the elongate shaft, and a distal end of the three-bar linkage is coupled to an end effector. The end effector can be, for example, a grasper, a biopsy probe, a snare loop, forceps, scissors, a needle knife, a sphincterotome, etc. In use, the three-bar linkage is adapted to laterally articulate relative to a longitudinal axis of the elongate shaft to allow the end effector to be angularly oriented relative to the elongate shaft.

The three-bar linkage of the device can have a variety of configurations, but in one exemplary embodiment the three-bar linkage includes a first articulating link having a proximal end coupled to the distal end of the elongate shaft, a second articulating link having a proximal end pivotally coupled to a distal end of the first articulating link and a distal end coupled to the end effector, and a third articulating link having a proximal end pivotally coupled to an articulation actuator extending through the elongate shaft and a distal end pivotally coupled to the second articulating link. In another embodiment, the third articulating link can be a flexible wire that is adapted to buckle when a force is applied thereto to cause the second articulating link to pivot relative to the first articulating link. Alternatively, the third link can be a cam having a cam slot formed therein for receiving a pin formed on the second articulating link such that movement of the cam is effective to cause the second articulating link to pivot relative to the first articulating link.

The articulation actuator can also have a variety of configurations, but in one embodiment it is adapted to translate along a longitudinal axis of the elongate shaft to laterally articulate the second link and the end effector relative to the first link. In an exemplary embodiment, the articulation actuator is in the form of a hollow elongate tube. The articulation actuator can also be rotatable relative to the elongate shaft such that rotation of the articulation actuator rotates the three-bar linkage and the end effector relative to the elongate shaft. In other embodiments, the device can include an actuation wire extending through the elongate shaft and the three-bar linkage and adapted to translate along a longitudinal axis of the elongate shaft to actuate the end effector. The elongate shaft of the device can also optionally be flexible to allow the shaft to be inserted through a tortuous lumen.

In another embodiment, the end effector can be rotatably coupled to the three-bar linkage such that the end effector can rotate relative to the three-bar linkage. An actuation wire can extend through the elongate shaft and the three-bar linkage for rotating the end effector relative to the three-bar linkage. In other aspects, the three-bar linkage can be rotatably coupled to the elongate shaft such that the three-bar linkage and the end effector coupled thereto are adapted to rotate about a longitudinal axis of the elongate shaft.

In yet another embodiment, a manually articulating device is provided and includes an elongate shaft having proximal and distal ends, a first link having a proximal end coupled to the distal end of the elongate shaft, a second link having a proximal end pivotally coupled to a distal end of the first link and a distal end coupled to an end effector, and a third link having a distal end pivotally coupled to the second link. The device can also include an articulation actuator extending through the elongate shaft and having a distal end coupled to a proximal end of the third link. The articulation actuator can be adapted to translate along a longitudinal axis of the elongate shaft such that translation of the articulation actuator is adapted to laterally articulate the second link and the end effector relative to the first link and the elongate shaft.

In one exemplary embodiment, the end effector can be rotatably coupled to the second link. In another embodiment, the first link can be rotatably coupled to the elongate shaft such that the first link, second link, third link, and end effector can rotate about a longitudinal axis of the elongate shaft. The articulation actuator can be rotatable relative to the elongate shaft such that rotation of the articulation actuator is effector to rotate the first link, second link, third link, and end effector about a longitudinal axis of the elongate shaft.

In other embodiments, proximal movement of the articulation link can be adapted to laterally articulate the second link and the end effector in a first lateral direction, and distal movement of the articulation link is adapted to longitudinally align the second link and the end effector with the longitudinal axis of the elongate shaft. In particular, proximal movement of the articulation link can be effective to move the third link proximally, which causes the second link to pivot relative to the first link.

Exemplary surgical methods are also provided, and in one embodiment the method can include inserting an elongate shaft of a surgical device through a body lumen to position an end effector located at a distal end of the elongate shaft adjacent to tissue to be treated. An articulation actuator can be translated along a longitudinal axis of the elongate shaft to cause a three-bar linkage to laterally articulate the end effector in a direction substantially perpendicular to a longitudinal axis of the elongate shaft to allow the end effector to be angularly oriented relative to the elongate shaft. The method can also include rotating the end effector relative to the elongate shaft. In one embodiment, the three-bar linkage can rotate with the end effector relative to the elongate shaft. For example, the articulation actuator can be rotated relative to the elongate shaft to rotate both the three-bar linkage and the end effector. In another embodiment, the end effector can rotate relative to the three-bar linkage. For example, an actuation wire coupled to the end effector and extending through the elongate shaft and the three-bar linkage can be rotated.

BRIEF DESCRIPTION OF THE DRAWINGS

The invention will be more fully understood from the following detailed description taken in conjunction with the accompanying drawings, in which:

FIG. 1A is a perspective view of one embodiment of an insertion portion of a manually articulating device having an end effector with grasper jaws;

FIG. 1G is an exploded view of yet another embodiment of a three-bar linkage;

FIG. 1H is an assembled view of the three-bar linkage shown in FIG. 1G;

FIG. 2A is a perspective view of another embodiment of an end effector having opposed biopsy jaws and a spike for use with a manually articulating device;

FIG. 3B is an exploded view of the handle portion shown in FIG. 3A;

FIG. 4C is an exploded view of the insertion portion shown in FIG. 4B;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for controlling movement of a working end of a surgical device, and in particular for performing various surgical procedures using an instrument having an end effector that can be articulated relative to an elongate shaft of the device. In certain embodiments, the end effector can also optionally rotate relative to the elongate shaft of the device, and/or the shaft can rotate relative to a handle of the device. Articulation and rotation of the end effector will allow the end effector to be positioned at various locations during a surgical procedure, thereby providing the user with precise control over the end effector. A person skilled in the art will appreciate that the present invention has application in endoscopic procedures, laparoscopic procedures, and in conventional open surgical procedures, including robotic-assisted surgery.

Figure 1B:
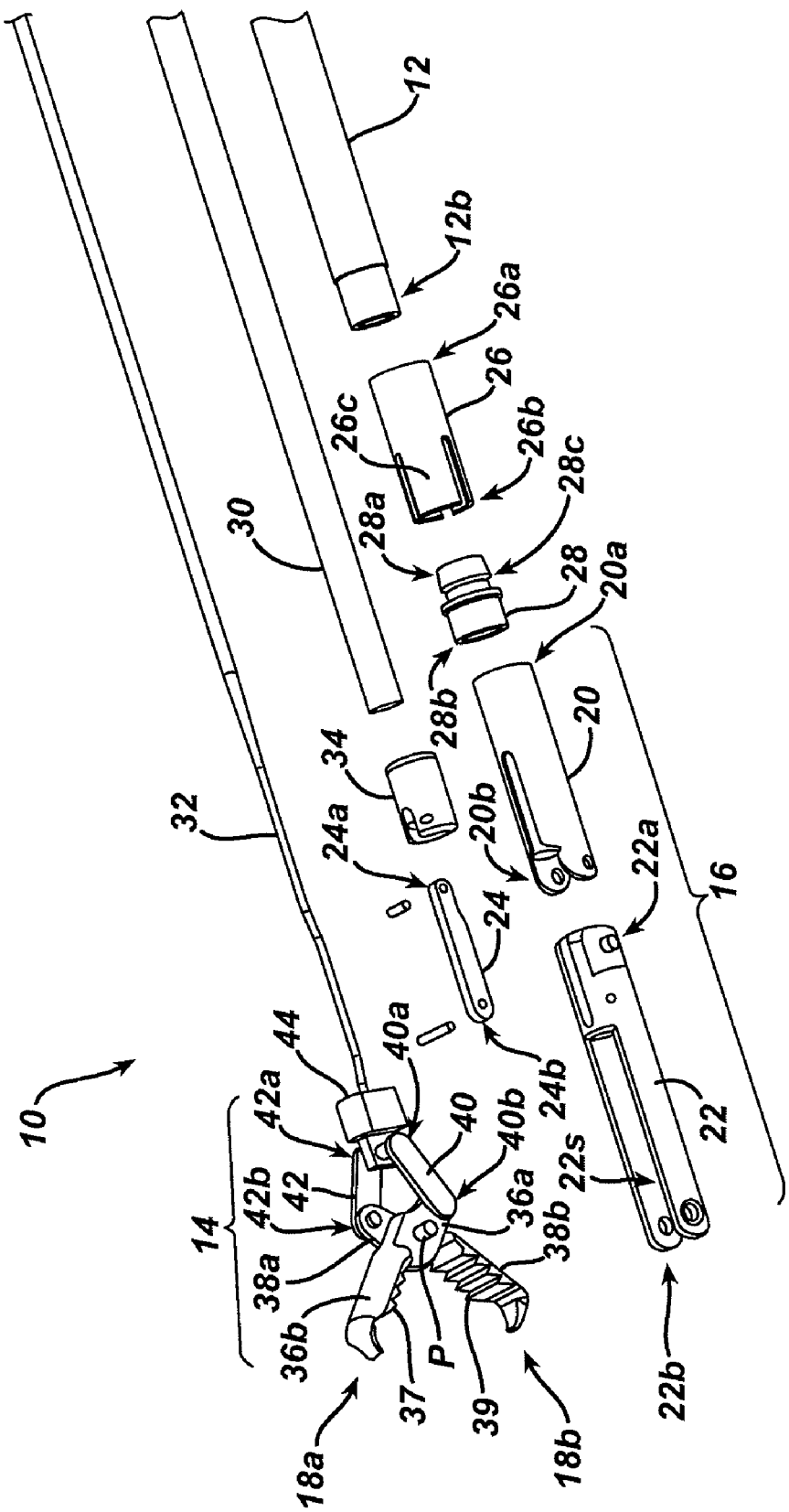
FIG. 1B is an exploded view of the insertion portion of the surgical device of FIG. 1A.

FIGS. 1A and 1B illustrate one exemplary embodiment of an insertion portion 10 of a manually articulating device. A handle portion of the device will be discussed in more detail below with respect to FIGS. 3A-3D. The insertion portion 10 is preferably configured to be inserted into a patient's body, and it can be rigid for laparoscopic applications, flexible for endoscopic applications, or it can have rigid and flexible portions as may be desired. As shown, the insertion portion 10 generally includes a hollow elongate shaft 12 having a working end or end effector 14 coupled to a distal end 12b thereof by a three-bar linkage 16. While the end effector 14 can have various configurations, as will be discussed in more detail below, in the illustrated embodiment the end effector 14 is in the form of graspers having opposed jaws 18a, 18b that are pivotally coupled to one another. The three-bar linkage 16 allows the end effector 14 to be oriented at an angle relative to a longitudinal axis L of the elongate shaft 12. The device can also optionally be configured to allow the end effector 14 to rotate relative to and about the longitudinal axis L of the elongate shaft 12. In the illustrated embodiment, the three-bar linkage 16 is rotatably coupled to the distal end 12b of the elongate shaft 12, and thus the three-bar linkage 16, as well as the end effector 14 coupled thereto, can be positioned in various axial orientations. The location of the rotation joint R proximal of the articulation joint A is particularly advantageous in that rotation of the end effector 14 can change the location of the plane within which the end effector 14 articulates.

Figure 1C:
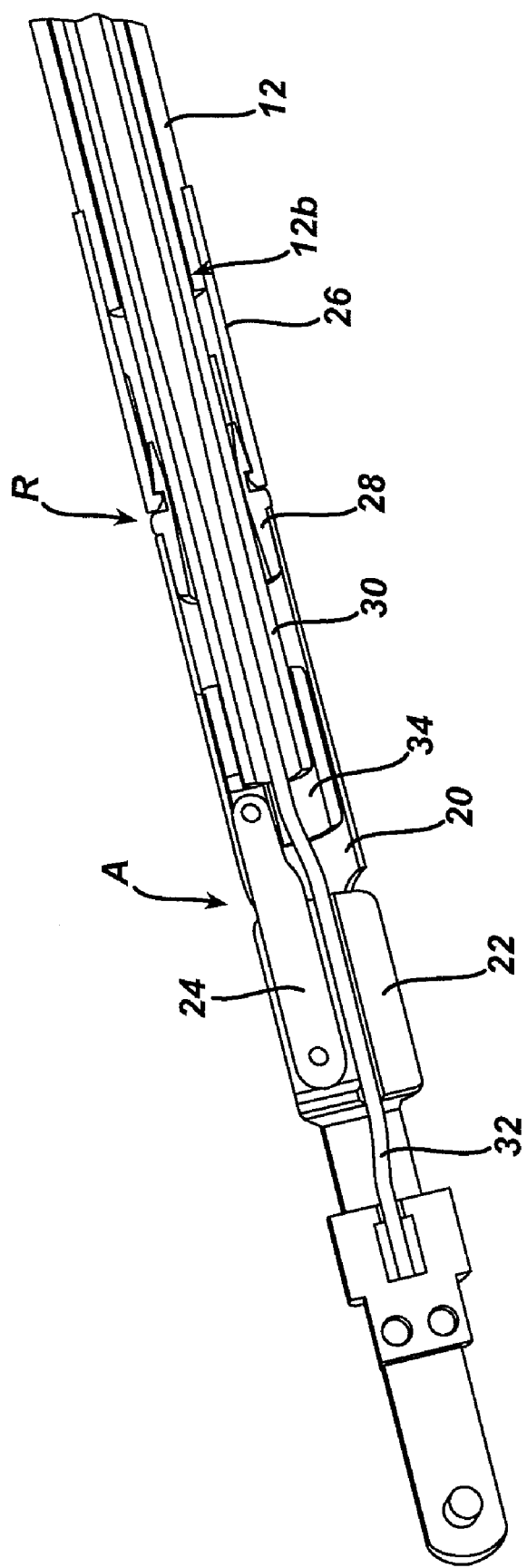
FIG. 1C is cross-sectional view of the insertion portion of the surgical device of FIG. 1A.
Figure 1D:
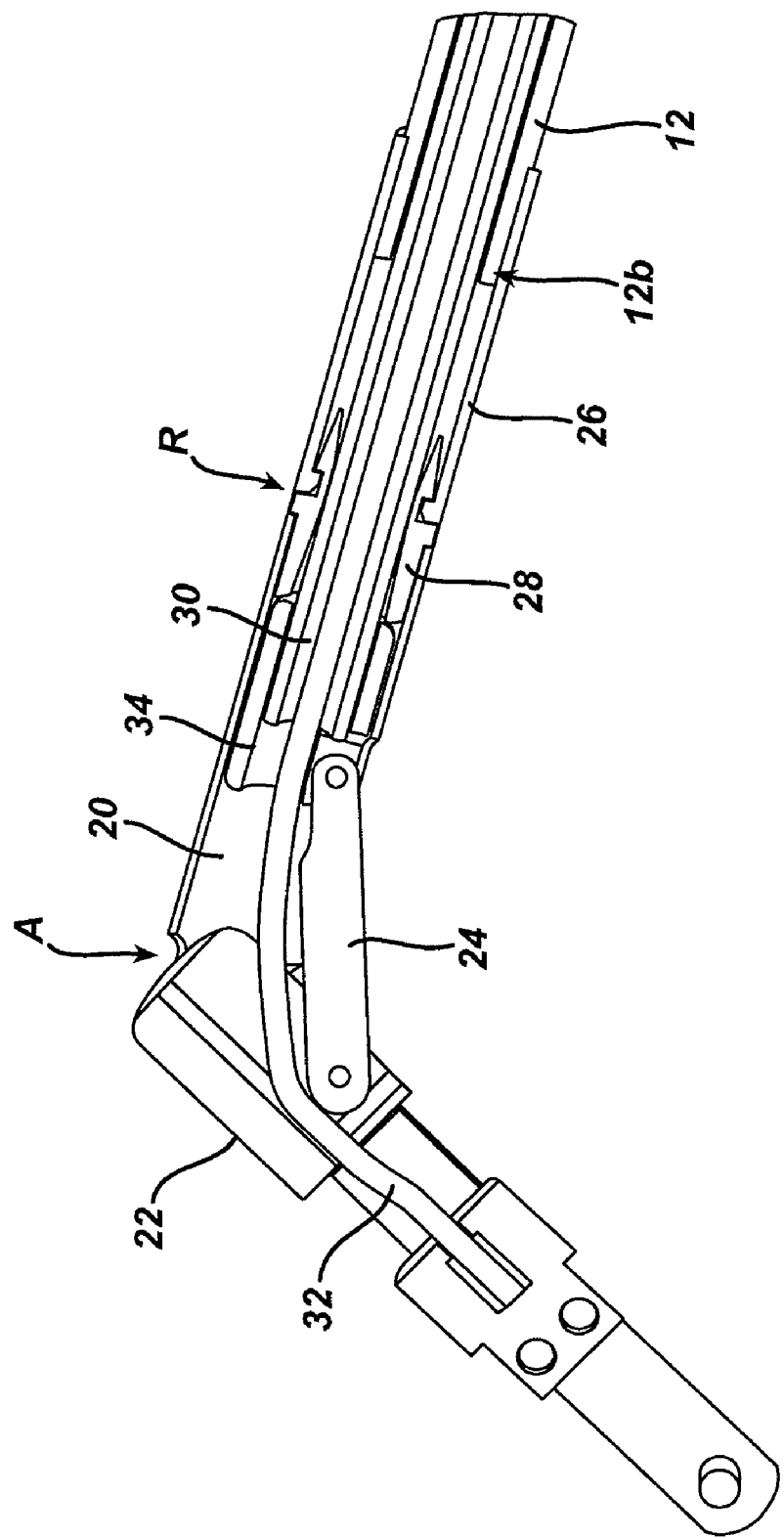
FIG. 1D is a cross-sectional view of the insertion portion of the surgical device of FIG. 1A, showing a three-bar linkage articulated to position an end effector of the device at an angle relative to an elongate shaft of the device.

The three-bar linkage 16 can have a variety of configurations, but in an exemplary embodiment, as shown in more detail in FIGS. 1B and 1D, it includes three links 20, 22, 24 that are pivotally coupled to one another. Each link can have a variety of configurations, but in an exemplary embodiment the first and second links 20, 22 each have a generally hollow elongate shape and the third link 24 is in the form of an elongate rod or bar. The first link 20 can have a proximal end 20a that is coupled to a distal end 12b of the elongate shaft 12 via first and second rotation couplings 26, 28, which will be discussed in more detail below. The distal end 20b of the first link 20 can be pivotally coupled to a proximal end 22a of the second link 22, e.g., by a pivot joint. The distal end 22b of the second link 22 can in turn be coupled to the end effector 14, which will be discussed in more detail below. The third link 24 can extend at least partially through the first and second links 20, 22, and it can have a distal end 24b that is pivotally coupled to the second link 22, e.g., by a pivot pin, to form a three-bar linkage mechanism. The particular location at which the third link 24 mates to the second link 22 can vary, but it is preferably pivotally mated at a location that will allow the third link 24 to apply a force to the second link 22 to cause the second link 22 to articulate relative to the first link 20. The proximal end of the third link 24 can be coupled to an articulation actuator 30 extending through the elongate shaft 12 and at least partially through the first link 20. The articulation actuator 30 can have a variety of configurations, but in an exemplary embodiment the articulation actuator 30 is in the form of a hollow elongate shaft or tube. Such a configuration allows an actuation wire 32 to extend therethrough for actuating the end effector 14, as will be discussed below. FIG. 1B also illustrates an articulation coupling 34 for connecting the articulation actuator 30 to the third link 24. The coupling 34 is merely a tubular member that fixedly mates to the articulation actuator 30 and pivotally mates to the third link 34. A person skilled in the art will appreciate that the articulation actuator 30 can be directly mated to the third link 24.

In use, proximal movement of the articulation actuator 30 relative to and along the longitudinal axis L of the elongate shaft 12 will apply a proximally-directed force to the third link 24. The third link 24 will thus apply a proximally-directed force to the second link 22, causing the second link 22 to pivot laterally relative to the longitudinal axis L of the elongate shaft 12. As a result, the second link 22, with the end effector 14 coupled thereto, will move laterally in a single plane to allow the end effector 14 to extend at an angle relative the longitudinal axis L of the elongate shaft 12, as shown in FIG. 1D. The end effector 14 can be returned to the original, longitudinally-aligned position, shown in FIGS. 1A and 1C, by moving the articulation actuator 30 distally relative to the elongate shaft 12.

As previously indicated, in addition to articulating movement, the end effector 14 can also be configured to rotate relative to the elongate shaft 12, thus allowing the end effector 14 to be positioned in multiple angular orientations. The particular location of the rotation joint R can vary, and it can be located proximal to the three-bar linkage 16, at a mid-portion of the three-bar linkage 16, or distal to the three-bar linkage 16. In an exemplary embodiment, the rotation joint R is located proximal to the three-bar linkage 16, and more preferably proximal to the articulation joint A formed between the first and second links 20, 22. As shown in FIGS. 1A-1D, the first link 20 can be rotatably coupled to the distal end 12b of the elongate shaft 12 by one or more rotation couplings. The illustrated embodiment includes first and second rotation couplings 26, 28. The first rotation coupling 26 has a generally elongate hollow shape with a proximal end 26a that is fixedly mated to the elongate shaft 12 and a distal end 26b having deflectable tabs 26c formed therearound. The tabs 26c can be formed by longitudinally-extending cut-outs formed in and spaced radially around the distal end 26b of the first rotation coupling 26. Each tab 26c can include an annular flange or lip (not shown) formed on an inner surface thereof. The second rotation coupling 28 can also have a generally elongate hollow shape, and it can include a groove or cut-out 28c formed therein. The first and second rotation couplings 26, 28 can be mated by advancing the tabs 26c over the proximal end 28a of the second rotation coupling 28. The tabs 26c will deflect until the annular flange or lip on the tabs 26c extends into and engages the groove 28c formed in the second rotation coupling 28. The two rotation couplings 26, 28 can thus rotate relative to one another, allowing the first link 20, which is fixedly mated to the distal end 28b of the second rotation coupling 28, to rotate relative to the first rotation coupling 26 and the elongate shaft 12.

Rotation of the articulation actuator 30 can be achieved by rotating the articulation actuator 30. In particular, rotation of articulation actuator 30 relative to and about the longitudinal axis L of the elongate shaft 12 will rotate the third link 24, which is coupled to the second link 22, which in turn is coupled to the end effector 14 and the first link 20. As a result, the entire three-bar linkage 16 will rotate with the end effector 14 relative to and about the longitudinal axis L of the elongate shaft 12. Rotation can also be done while the end effector 14 is articulated, thereby changing the plane within which the end effector 12 articulates.

Figure 1E:
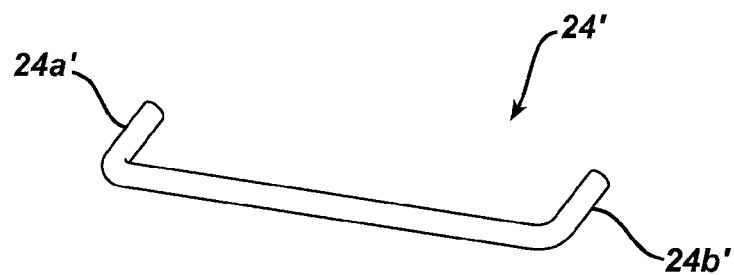
FIG. 1E is a perspective view of a link for use with a three-bar linkage in accordance with another embodiment of the present invention.
Figure 1F:
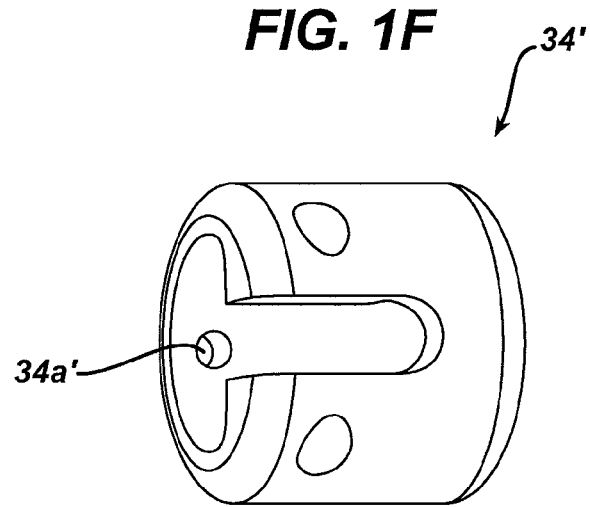
FIG. 1F is a perspective view of an articulating coupling configured for use with the link of FIG. 1E.

FIGS. 1E-1H illustrate alternative embodiments of a three-bar linkage. In one embodiment, shown in FIGS. 1E-1F, the third link 24 of FIGS. 1B and 1D can be replaced with a flexible link. While the flexible link can have a variety of configurations, and it can be in the form of a flexible cable or similar member, FIG. 1E illustrates a flexible wire 24'. As shown, the wire 24' has a generally elongate shape with first and second terminal ends 24a', 24b' that are bent to extend at an angle, e.g., 90°, relative to the remainder of the wire 24'. The ends 24a', 24b' are configured to replace the pivot pins used to pivotally couple the third link 24 to the first and second links 20, 22 of the embodiment shown in FIGS. 1A-1D. Thus, the ends 24a', 24b' can extend into and pivotally couple to the first and second links 20, 22 (FIGS. 1B-1D) to allow the first, second, and third links 20, 22, 24' to pivot relative to one another. In use, proximal movement of the articulation actuator 30 relative to and along the longitudinal axis L of the elongate shaft 12 will apply a proximally-directed force to the third link 24'. The third link 24' will thus flex or buckle, thereby causing the second link 22 to pivot laterally relative to the longitudinal axis L of the elongate shaft 12. As a result, the second link 22, with the end effector 14 coupled thereto, will move laterally in a single plane to allow the end effector 14 to extend at an angle relative the longitudinal axis L of the elongate shaft 12. The end effector 14 can be returned to the original, longitudinally-aligned position, shown in FIGS. 1A and 1C, by releasing the articulation actuator 30 to allow the flexible link 24' to return to its original, non-flexed position shown in FIG. 1E, thereby forcing the articulation actuator 30 to move distally relative to the elongate shaft 12. The flexible link 24' can also be used to transfer rotational forces to effect rotation of the end effector, but in an exemplary embodiment the articulating coupling 34 (FIGS. 1B-1D) is modified to be non-rotatably coupled to the first link 20. As shown in FIG. 1F, which illustrates an alternative embodiment of an articulating coupling 34', this can be achieved by inserting a pin member (not shown) through a bore 34a' formed in the articulating coupling 34', and positioning the pin member such that it is slidably disposed within a longitudinal slot (not shown) formed in the first link 20. As a result, when the articulation actuator 30 is rotated relative to and about the longitudinal axis L of the elongate shaft 12, the articulating coupling 34' will rotate therewith, thereby causing the first and second links 20, 22 to rotate, as well as the end effector 14. As a result, the entire three-bar linkage 16 will rotate with the end effector 14 relative to and about the longitudinal axis L of the elongate shaft 12. Rotation can also be done while the end effector 14 is articulated, thereby changing the plane within which the end effector 12 articulates.

FIGS. 1G-1H illustrate another embodiment of a three-bar linkage that is similar to the three-bar linkage shown in FIGS. 1A-1D. However, in this embodiment a cam 24" replaces both the third link 24 and the articulating coupling 34 of the previous embodiment. As shown in FIG. 1G, the cam 24" is generally hook-shaped and includes a curved slot 24a" formed therein. A proximal end 24p" of the cam 24" can be fixedly mated to the distal end of the articulation actuator 30, and a pin 25" can be slidably disposed through the slot 24a". The pin 25" can be fixedly mated to or formed on an inner wall of the third link 22. As with the embodiment shown in FIGS. 1B-1D, the first and second links 20", 22" can be pivotally coupled to one another. In FIG. 1G, the second link 20" is similar to link 20 of FIGS. 1B-1D, however link 20" has opposed bores spaced 20a", 20b" spaced a distance apart from the distal end 20d" of the link 20" for receiving opposed pins (only one pin 22" is shown) formed on the proximal end 22a of the second link 22. In use, as shown in FIG. 1H, distal movement of the articulation actuator 30 will move the cam 24" distally. As the cam 24" is moved relative to the pin 25", the cam slot 24a" will force the pin 25" to follow the path of the slot 24a". As a result, the second link 22 is caused to pivot laterally relative to a longitudinal axis of the elongate shaft (not shown). As a result, the second link 22, with the end effector (not shown) coupled thereto, will move laterally in a single plane to allow the end effector to extend at an angle relative the longitudinal axis of the elongate shaft. The end effector can be returned to the original, longitudinally-aligned position by moving the articulation actuator 30 proximally and thereby pulling the cam 24" proximally. Again, the cam slot 24a" will cause the pin 25" to slid therein and follow the path of the slot 24a", thus causing the second link 22 to return to its original, longitudinally aligned position.

Returning to the embodiment of FIGS. 1A-1D, as indicated above, the end effector 14 of the device can have various configurations but in the embodiment shown in FIGS. 1A and 1B the end effector 14 is in the form of a grasper having opposed jaws 18a, 18b. As best shown in FIG. 1B, each jaw 18a, 18b includes a distal portion 36b, 38b having series of teeth 37, 39 formed thereon for grasping tissue, and a proximal portion 36a, 38a that pivotally mates to a distal end 40b, 42b of an actuation link 40, 42. The jaws 18a, 18b are pivotally mated to one another at a pivot point P located between the proximal and distal portions 36a, 38a, 36b, 38b. The distal end 24b of the second link 24 is also mated to the opposed jaws 18a, 18b at the pivot point P. The proximal end 40a, 42a of each actuation link 40, 42 is pivotally mated to an actuation pusher 44. The particular configuration of the actuation pusher 44 can vary, but in an exemplary embodiment the actuation pusher 44 has a generally rectangular configuration and is slidably disposed within and between opposed slots 22s formed in a distal portion of the second link 22. Such a configuration will prevent independent rotation of the actuation pusher 44 relative to the second link 22. The actuation wire 32 can have a variety of configurations, but in an exemplary embodiment it is an elongate flexible cable or wire that extends through second link 22, the articulating coupling 34 which is disposed within the second link 22, and the articulation actuator 30.

In use, proximal movement of the actuation wire 32 relative to the elongate shaft 12 will pull the actuation pusher 44 proximally within the slots 22c formed in the second link 22. The actuation links 40, 42 will thus be pulled proximally, bringing the proximal and distal portions 36a, 38a, 36b, 38b of each jaw 18a, 18b toward one another to thereby close the jaws 18a, 18b. Conversely, distal movement of the actuation wire 32 within the slots 22c formed in the second link 22 will move the actuation pusher 44 distally, which will cause the links 40, 42 and the proximal and distal portions 36a, 38a, 36b, 38b of the jaws 18a, 18b to pivot laterally outward, thereby opening the jaws 18a, 18b.

Figure 2B:
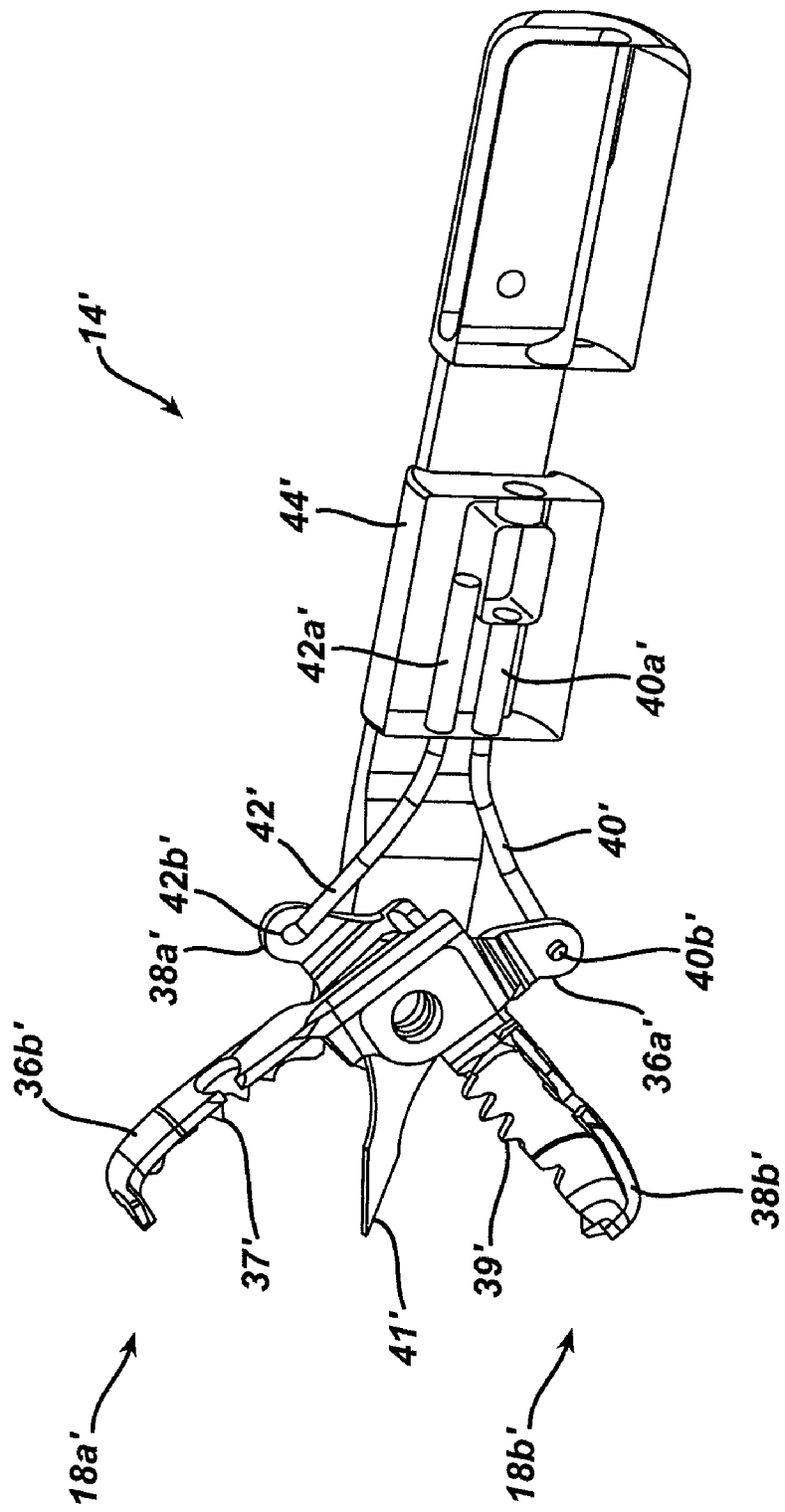
FIG. 2B is a cross-sectional view of the end effector of FIG. 2A.

FIGS. 2A-2B illustrate an alternative embodiment of mechanism for opening and closing opposed jaws. In this embodiment, the end effector 14' is in the form of biopsy jaws. The jaws 18a', 18b' are similar to the jaws 18a, 18b described above with respect to FIG. 1B, however each jaw 18a', 18b' has a generally hollow configuration with teeth 37', 39' formed around a perimeter of the distal portion 36b', 38b' for allowing the jaws 18a', 18b' to essentially bite off and remove a tissue sample. In this embodiment, the actuation links are replaced with pull wires 40', 42'. Each pull wire 40', 42' has a distal end 40b', 42b' that is coupled to the proximal portion 36a', 36b' of a jaw 18a', 18b', and a proximal end 40a', 42a' that is disposed within and fixedly coupled to the actuation pusher 44'. As with the previous embodiment, proximal movement of the actuation wire and thus the actuation pusher 44' will pull the wires 40', 42' proximally to close the jaws 18a', 18b', and distal movement of the actuation wire and thus the actuation pusher 44' will push the wires 40', 42' distally to open the jaws 18a', 18b'.

Figure 3A:
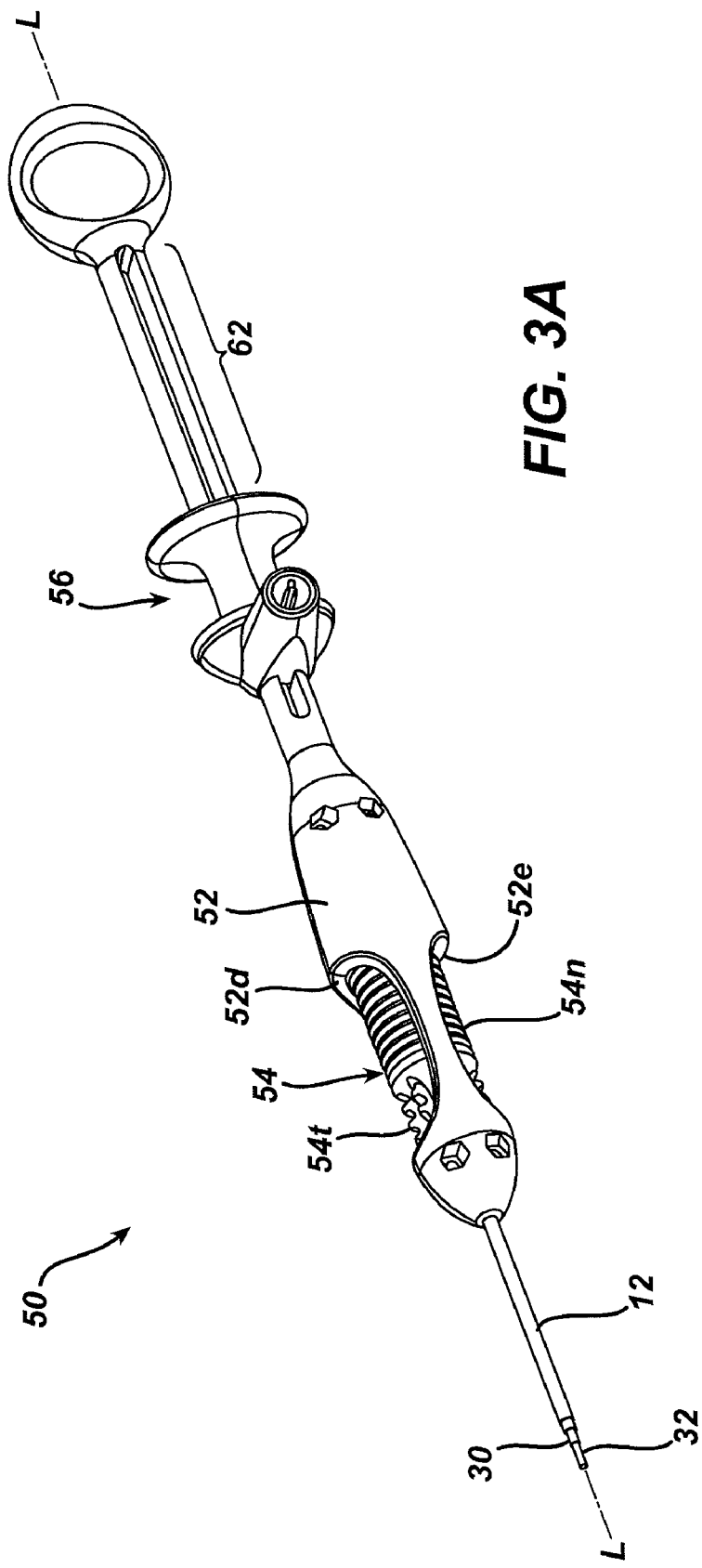
FIG. 3A is a perspective view of one embodiment of a handle portion of a manually articulating device.

As previously indicated, the device can also include a handle coupled to the proximal end of the elongate shaft and having various controls formed thereon for controlling and manipulating the device. A person skilled in the art will appreciate that the particular configuration of the handle can vary, and that various techniques known in the art can be used for effecting movement of various portions on the device. FIGS. 3A-3D illustrate one exemplary embodiment of a handle 50 for use with the insertion portion 10 of the device shown in FIG. 1A. As shown, the handle 50 has a generally elongate cylindrical configuration to facilitate grasping thereof. The handle housing 52 can have an integral or unitary configuration, or it can be formed from two housing halves 52a, 52b that mate to enclose various components therein. The housing halves 52a, 52b are shown in FIG. 3B. The various component disposed within the handle housing 52 can also vary, but in an exemplary embodiment the handle includes an articulation knob 54 for articulating and rotating the end effector 14, and an actuation knob 56 for actuating the end effector 14.

Figure 3C:
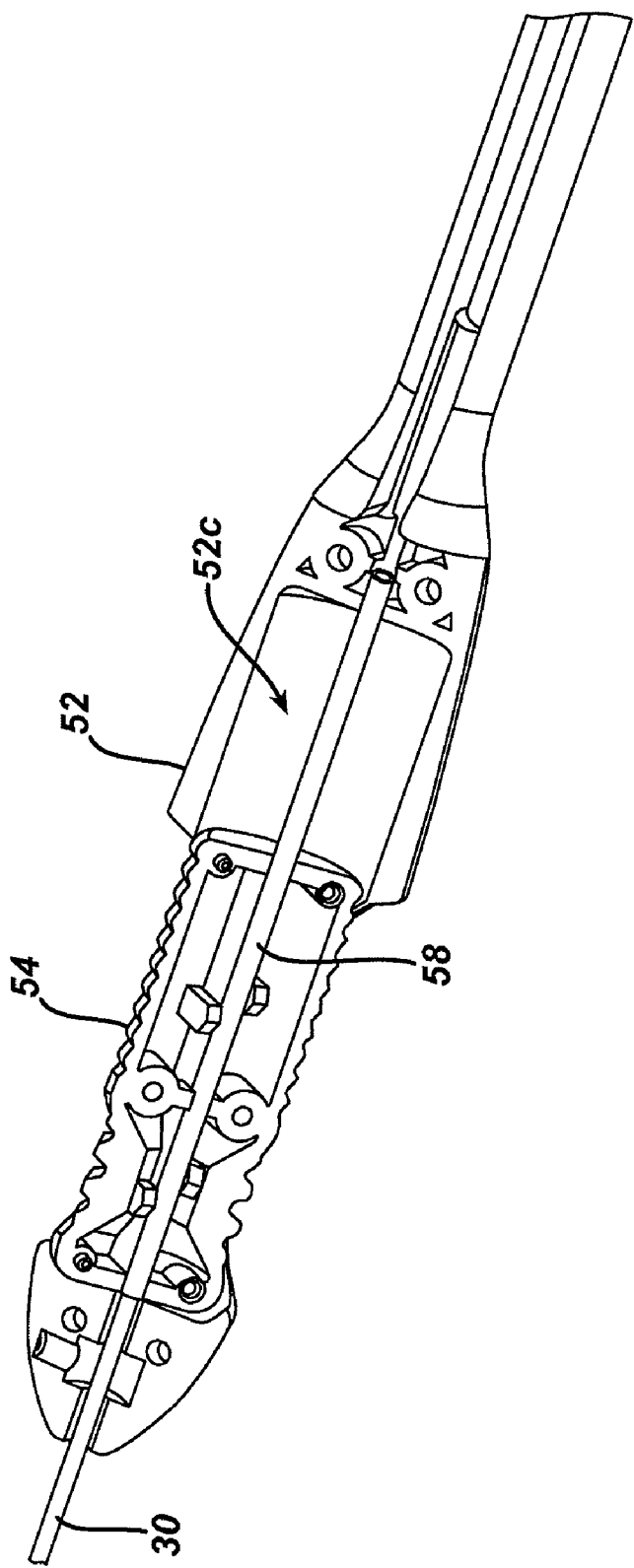
FIG. 3C is a cross-sectional view of articulation mechanism of the handle portion shown in FIG. 3A.

The articulation knob 54 is shown in more detail in FIGS. 3B and 3C, and as shown the knob 54 has a generally cylindrical configuration. The knob 54 can have an integral or unitary configuration, or it can be formed from two halves 54a, 54b that mate together, as shown. The proximal end 30a of the articulation actuator 30 can mate to the knob 54 such that rotation and translation of the knob 54 will cause corresponding rotation and translation of the articulation actuator 30, thereby rotating and articulating the end effector 14, as previously described. While various techniques can be used to mate the articulation actuator 30 to the articulation knob 54, in an exemplary embodiment the articulation knob 54 includes an axle 58 fixedly disposed therein and engaged between the knob halves 54a, 54b. The articulation actuator 30 extends through an inner lumen of the axle 58 and is fixedly mated thereto. Various mating techniques can be used to mate the articulation actuator 30 to the axle 58 including, for example, an interference or compression fit, an adhesive, or other mechanical or chemical mating techniques known in the art.

In order to translate and rotate the articulation knob 54, the handle housing 52 can include an elongate cavity 52c (FIG. 3B) formed therein that slidably and rotatably receives the knob 54. The handle housing 52 can also include one or more cut-outs formed therein for allowing a user to access the knob. FIG. 3A illustrates opposed cut-outs 52d, 52e formed in the handle housing 52. The articulation knob 54 can also include features to facilitate movement thereof. For example, the articulation knob 54 can include one or more surface features formed on an external surface thereof for allowing the user to more easily grasp the knob. In the illustrated embodiment, the knob 54 includes a series of ridges 54r formed therein, as well as a series of longitudinally-oriented teeth 54b formed on a portion thereof. The ridges 54r can provide a detent feature to maintain the position of the articulation. A corresponding detent snap can be located in the cavity 52c.

In use, the knob 54 can be grasped by a user and rotated about its longitudinal axis (i.e., about the longitudinal axis L of the shaft 12 and handle 50). Rotation of the knob will cause corresponding rotation of the axle 58 and the articulation actuator 30. The actuation wire 32, which extends through the articulation actuator 30, will not rotate with the articulation actuator 30 since it is not coupled thereto. As previously explained, rotation of the articulation actuator 30 will cause corresponding rotation of the three-bar linkage 16 and the end effector 14 coupled thereto. The articulation knob 54 can also be slid or translated longitudinally along its axis L, and within the elongate cavity 52c formed in the handle housing 52. Proximal movement of the articulation knob 54 within the handle housing 52 will pull the articulation actuator 30 proximally, thereby articulating the end effector 14, as previously explained. Distal movement of the articulation knob 54 within the handle housing 52 will in turn move the articulation actuator 30 distally, thereby returning the end effector 14 to its original longitudinally-aligned position.

Figure 3D:
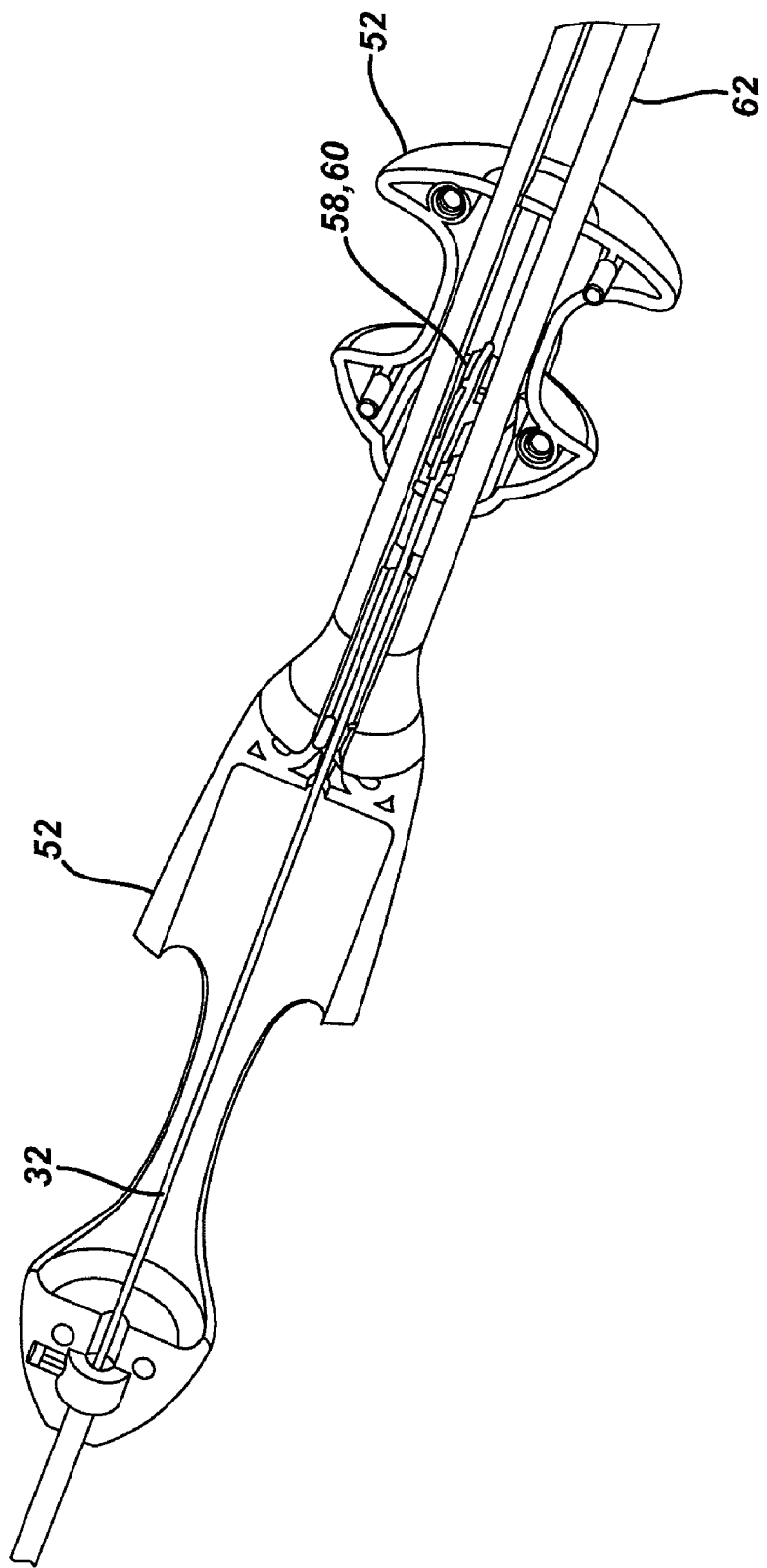
FIG. 3D is a cross-sectional view of an actuation mechanism of the handle portion shown in FIG. 3A.

As indicated above, the device can also include an actuation knob 56 for actuating the end effector 14 (i.e. for firing, opening and closing, energizing, etc,). The actuation knob 56 can have a variety of configurations, but in the illustrated embodiment the knob 56 has a bar-bell shape. The knob 56 can have an integral or unitary configuration, or it can be formed from two halves 56a, 56b that mate together, as shown in FIG. 3B. The proximal end 32a of the actuation wire 32 can mate to the actuation knob 56 such that translation of the knob 56 will cause corresponding translation of the actuation wire 32, thereby actuating the end effector 14 as previously described. While various techniques can be used to mate the actuation wire 32 to the actuation knob 56, in an exemplary embodiment the proximal end 32a of the actuation wire 32 includes a bend 32x formed therein for mating to first and second retainer members 59, 60. The retainer members 59, 60, which engage the bend 32x in the wire 32 therebetween, can be disposed within and mated to the actuation knob 56, as shown in FIG. 3D.

In order to translate the actuation knob 56, the knob 56 can include an inner lumen extending longitudinally therethrough and it can be slidably disposed around an elongate shaft portion 62 of the handle housing 52. In use, the knob 56 can be grasped by a user and translated along the shaft portion 62 of the handle housing 52. Proximal movement of the actuation knob 56 along the shaft portion 62 will pull the actuation wire 32 proximally, thereby opening the jaws 18a, 18b of the end effector 12 as previously explained. Distal movement of the actuation knob 56 along the shaft portion 62 will in turn move the actuation wire 32 distally, thereby moving the jaws 18a, 18b to the closed position.

Figure 4A:
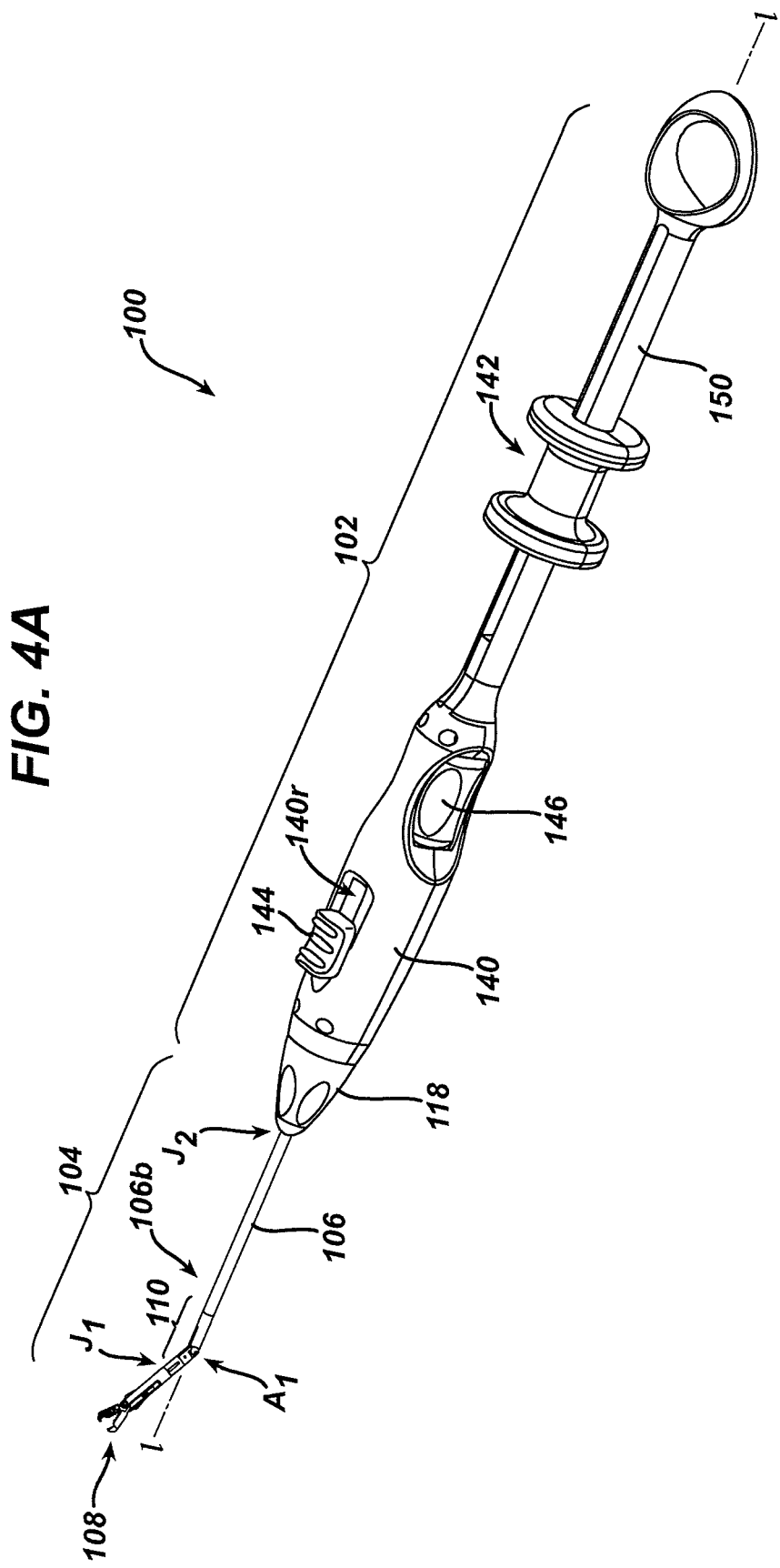
FIG. 4A is a perspective view of yet another embodiment of a manually articulating device having a handle portion and an insertion portion.

FIGS. 4A-4E illustrate another exemplary embodiment of a manually articulating device 100. The device is similar to the device shown in FIGS. 1A-1D and 3A-3D, however in this embodiment the device 100 has one articulation joint $A_1$ and two rotation joints $J_1$, $J_2$. In general, the device 100 includes a handle portion 102 and an insertion portion 104 having an elongate shaft 106 with an end effector 108 coupled to a distal end 106b thereof by a three-bar linkage 10. As with the previous embodiment, the three-bar linkage 110 includes an articulation joint A1 formed between first and second links 112, 114 for laterally articulating the second link 114, with the end effector 108 coupled thereto, relative to the longitudinal axis l of the elongate shaft 106. As with the previous embodiment, the device 100 can also include a rotation joint $J_1$ configured to allow the end effector 108 to rotate relative to and about the longitudinal axis l of the elongate shaft 108. In this embodiment, however, the rotation joint $J_1$ is located distal of the articulation joint $A_1$. As a result, the end effector 108 can rotate relative to the three-bar linkage 110. The location of a rotation joint $J_1$ distal to the articulation joint $A_1$ is particularly advantageous in that it allows the axial position of the end effector 108 to be oriented as desired after the end effector 108 has been articulated to a desired angle. The device 100 can also include a second rotation joint $J_2$. As shown in FIG. 4A, the elongate shaft 106 is rotatably coupled to a rotation knob 118 formed on the distal end of the handle 102. Thus, the entire shaft 106, as well as the three-bar linkage 110 and end effector 108 coupled thereto, can rotate relative to the handle 102. The location of the second rotation joint $J_2$ proximal of the articulation joint $A_1$ is particularly advantageous in that rotation of the end effector 108 can change the location of the plane within which the end effector 108 articulates.

Figure 4B:
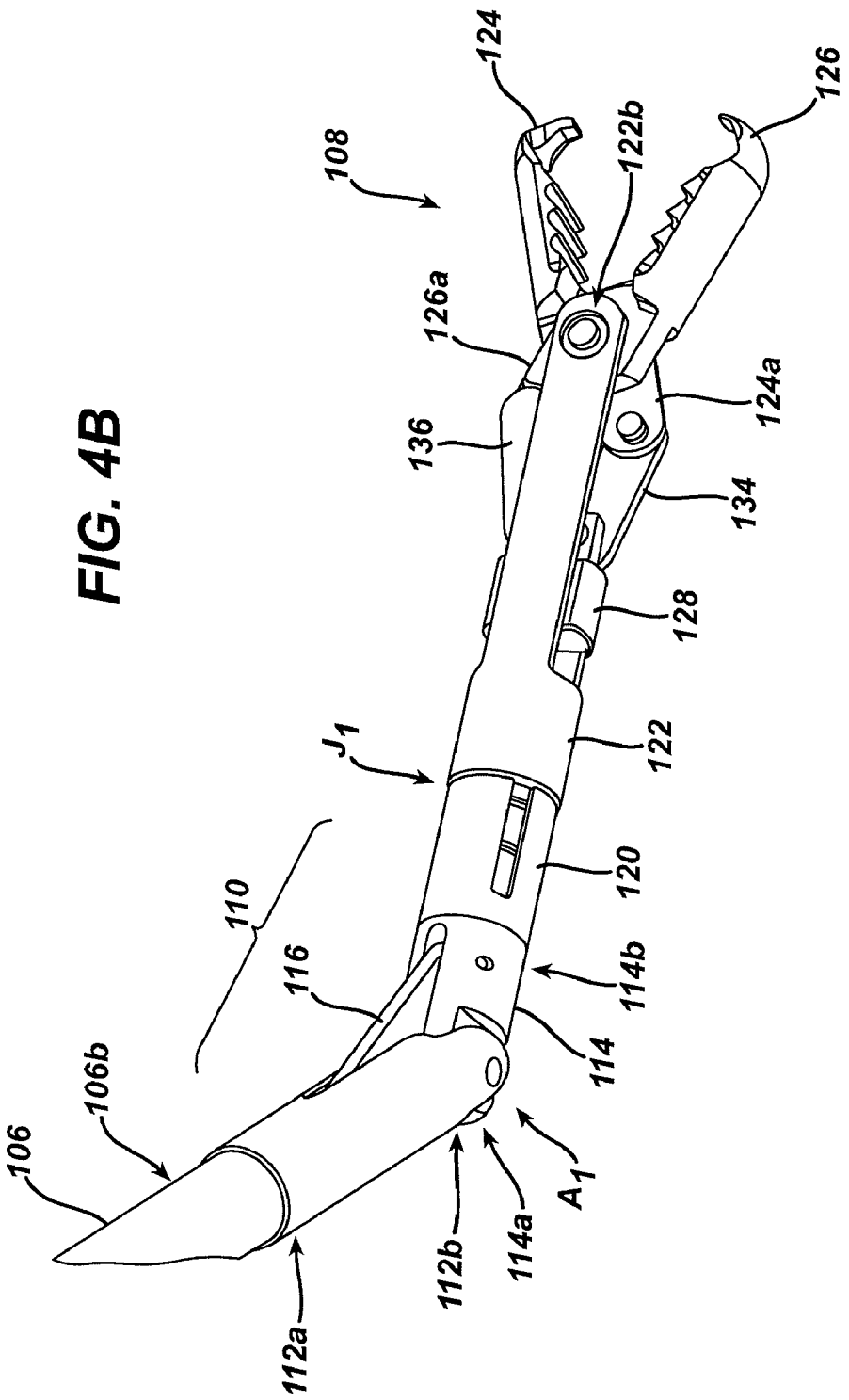
FIG. 4B is a perspective view of a distal end of the insertion portion of the device of FIG. 4A.

FIGS. 4B and 4C illustrate the three-bar linkage 110, i.e., the articulation joint $A_1$, and the first rotation joint $J_1$ in more detail. As shown, the three-bar linkage 110 is similar to the three-bar linkage previously described and generally includes first, second, and third links 112, 114, 116. In this embodiment, the first link 112 has a proximal end 112a that is fixedly mated to the distal end 106b of the elongate shaft 106, and a distal end 112b that is pivotally mated to a proximal end 114a of the second link 114. The distal end 114b of the second link 114 is coupled to the end effector 108 via a rotation coupling 120. Thus, unlike the previous embodiment where the distal end of the second link mated directly to the opposed jaws of the end effector, here the distal end 114b mates to a rotation coupling 120, which in turn mates to a clevis 122 that is mated to opposed jaws 124, 126 of the end effector 108. The rotation coupling 120 is similar to the rotation coupling 26 previously discussed, and generally includes flexible tabs 120t formed on the distal end thereof and having an annular flange or lip (not shown) formed on an inner surface thereof. The clevis 122 can have a generally elongate tubular configuration for receiving an actuation pusher 128 of the end effector 108 therein, as with the previous embodiment, and it can include a groove 122g formed in the proximal end thereof for receiving the annular lip formed in the rotation coupling 120. As a result, the rotation coupling 120 and the clevis 122 will rotatably mate relative to one another, thereby allowing the second link 114 to rotate relative to the clevis 122 and thus the end effector 108. As with the three-bar linkage 16 previously described, the second link 114 is also pivotally mated to a distal end 116b of the third link 116, and a proximal end 116a of the third link 116 mates to the articulation actuator 130. An articulation coupling 132 is shown for mating the third link 116 to the articulation actuator 130, however the third link 116 can optionally be directly mated to the distal end 130b of the articulation actuator 130.

FIGS. 4B and 4C also illustrate an end effector 108 that has a configuration similar to the end effector 14 previously described. In particular, the end effector 108 generally includes first and second jaws 124, 226 pivotally coupled to one another and to a distal end 122b of the clevis 122. First and second actuation links 134, 136 are pivotally coupled to a proximal portion 124a, 126a of the first and second jaws 124, 126, and an actuation pusher 128 is pivotally coupled to the first and second actuation links 134, 136. The actuation pusher 128 is slidably disposed within and extends between two opposed slots 122s formed in the clevis 122. An actuation wire 138 is coupled to the actuation pusher 128, and it is effective to translate axially relative to the articulation actuator 130 and the elongate shaft 106 to move the jaws 124, 126 between the open and closed positions. In this embodiment, the actuation wire 138 is also rotatable relative to the elongate shaft 106 and the articulation actuator 130. Rotation of the actuation wire 138 will cause the actuation pusher 128 to rotate, thereby causing the clevis 122 and the remainder of the end effector 108 to rotate relative to the rotation coupling 120.

Figure 4D:
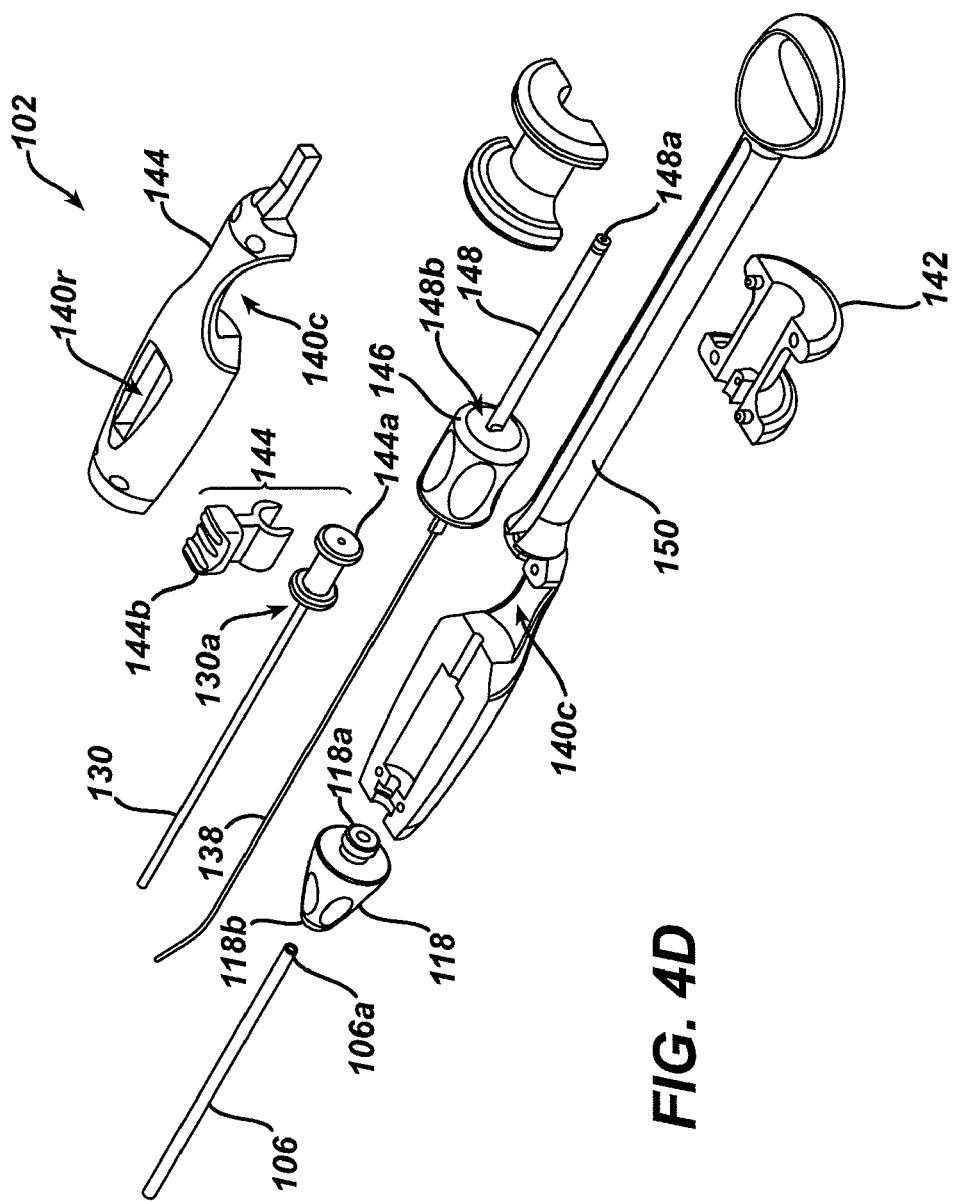
FIG. 4D is an exploded view of the handle portion of the device of FIG. 4A.
Figure 4E:
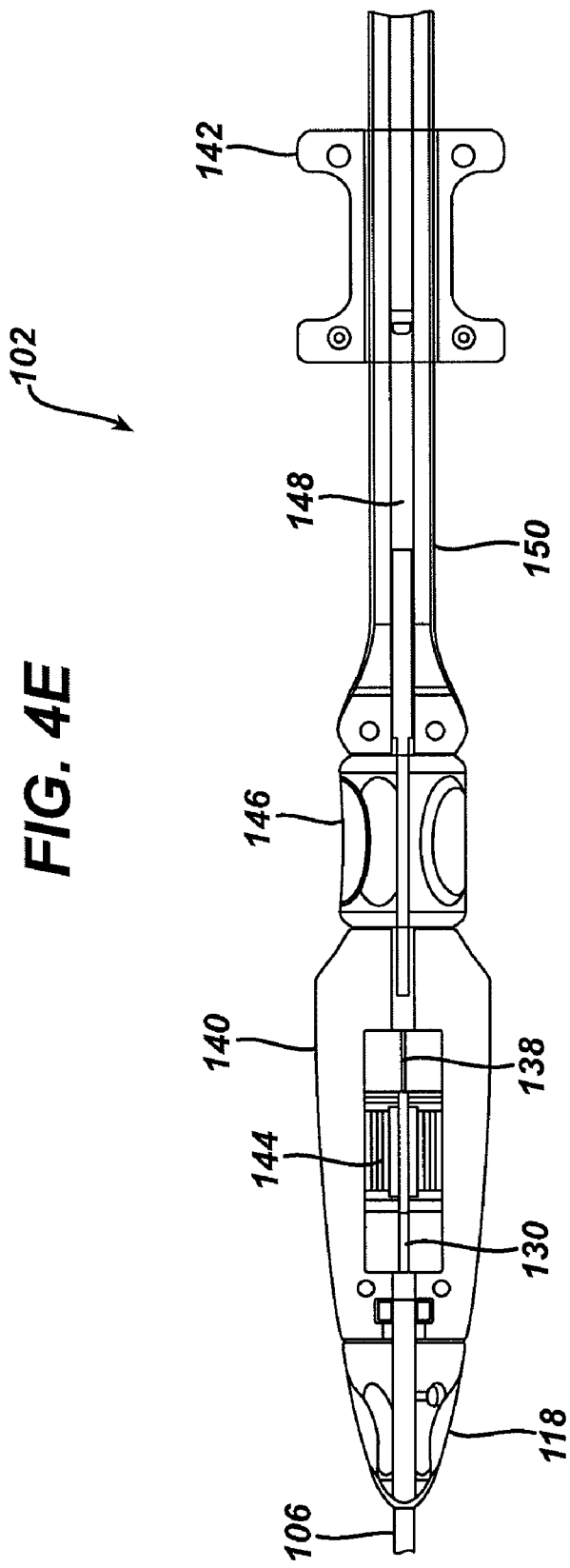
FIG. 4E is a cross-sectional view of the handle portion shown in FIG. 4A.

Referring back to FIG. 4A, the handle 102 can include certain features similar to the handle 50 previously described, including a handle housing 140 and an actuation knob 142. In this embodiment, the articulation knob 54 previously described with respect to FIGS. 3A-3C is replaced by two knobs: an articulation lever 144 and a rotation knob 146. The articulation lever 144 is slidably disposed within a cut-out 140r formed in the handle housing 140, and it is coupled to the proximal end of the articulation actuator. FIGS. 4D and 4E illustrate the handle 102 of the device 110 in more detail. While the articulation lever 144 can have a variety of configurations, in the illustrated embodiment the articulation lever 144 includes an articulation spool 144a that is fixedly mated to the proximal end 130a of the articulation actuator 130, and a button 144b that engages the spool 144a and that is adapted to be grasped by a user. In use, the button 144b extends through the cut-out 140r formed in the handle housing 140, thus allowing a user to grasp the button 144b and slide the lever 144 proximally and distally. Proximal movement of the articulation lever 144 will pull the articulation actuator 130 proximally, thereby causing the three-bar linkage 110 to articulation to position the end effector 108 at an angle relative to the longitudinal axis l of the elongate shaft 106, as previously described. Likewise, distal movement of the articulation lever 144 will return the three-bar linkage 110 to a longitudinally aligned position, thereby returning the end effector 108 to the longitudinally aligned position.

As indicated above, the handle 102 can also include a rotation knob 146 disposed therein. The rotation knob 146 can have a variety of configurations, but in an exemplary embodiment it is adapted to rotate axially relative to the handle housing 140 to rotate the actuation wire 138, and thereby rotate the end effector 108 relative to the second link 114. In the embodiment shown in FIGS. 4D and 4E, the rotation knob 146 is in the form of a generally cylindrical member that is rotatably disposed within a cylindrical cavity 140c formed in the handle housing 140. The knob 146 can include surface features, such as detents, formed thereon to facilitate grasping of the knob 146. As further shown, the knob 146 is disposed around a portion of an actuation spool 148. While not shown, the actuation spool 148 can be slidably but non-rotatably coupled to the rotation knob 146. This can be achieved by forming at least a portion of the spool 148 to have an asymmetrical shape that slidably and non-rotatably mates with an asymmetrical lumen extending through the actuation spool 148. Such a configuration allows the spool 148 to rotate with the rotation knob 14 and to translate with the activation knob 142, as discussed below. As further shown, a distal end 148b of the actuation spool 148 is fixedly mated to a proximal end of the actuation wire 138 such that rotation of the knob 146 will rotate the spool 148 and thus the actuation wire 138. The proximal end 148a of the actuation spool 148 is rotatably coupled to the actuation knob 142. The rotatable connection allows the actuation spool 148 to rotate with the rotation knob 146, while allowing the actuation knob 142 to remain in a fixed axial position. As with the previous embodiment, the actuation knob 142 is effective to translate along an elongate shaft portion 150 of the handle housing 140 to move the actuation wire 138 proximally and distally, thereby actuating the end effector 108, e.g., opening and closing the jaws. In this embodiment, the actuation knob 142 will pull the actuation spool 148, and thus the actuation wire 138 coupled thereto, proximally and distally relative to the handle housing 140. A person skilled in the art will appreciate that a single knob or lever can be used to effect both translation and rotation of the actuation wire, and that a variety of other techniques can in the art can be used instead of those shown in FIGS. 4D-4E.

As further shown in FIGS. 4D and 4E, the handle also includes a second rotation knob 118 coupled to a distal end of the handle housing 140. The second rotation knob 118 can have various configurations, but in the illustrated embodiment it has a generally cylindrical or conical configuration with surface features formed therearound to facilitate grasping. The knob 118 has a proximal end 118a that is rotatably coupled to the handle housing 140, and a distal end 118b that is fixedly mated to the proximal end 106a of the elongate shaft 106. In use, rotation of the second rotation knob 118 will rotate the elongate shaft 106 and thus the entire insertion portion 104 of the device 100. A person skilled in the art will appreciate that the second rotation joint $J_2$ can be formed at various other locations, including just proximal of the three-bar linkage 110 as previously shown in the embodiment of FIG. 1A.

Figure 5A:
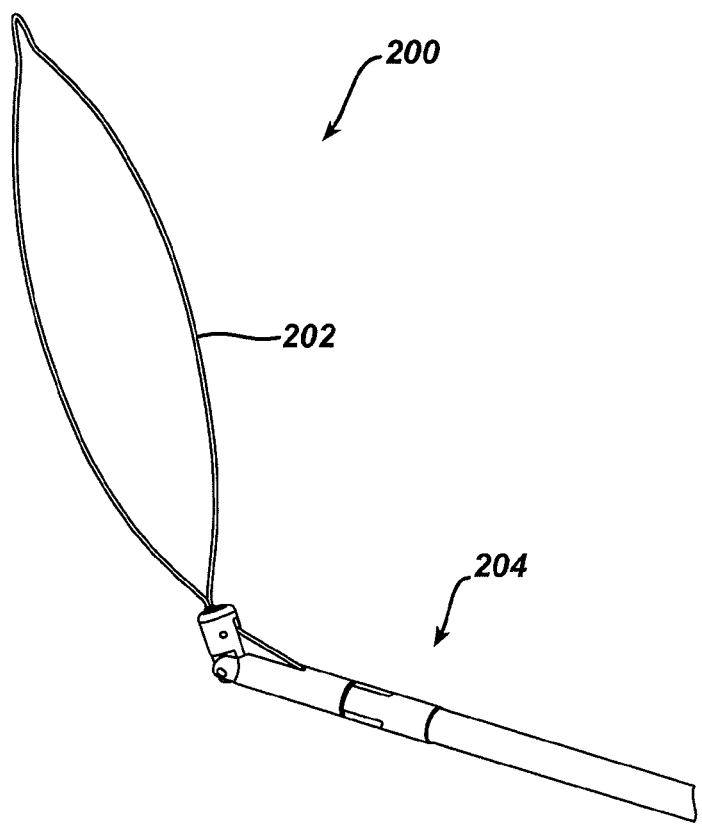
FIG. 5A is a perspective view of yet another embodiment of an insertion portion for use with a manually articulating device, showing an end effector with a snare loop.
Figure 5B:
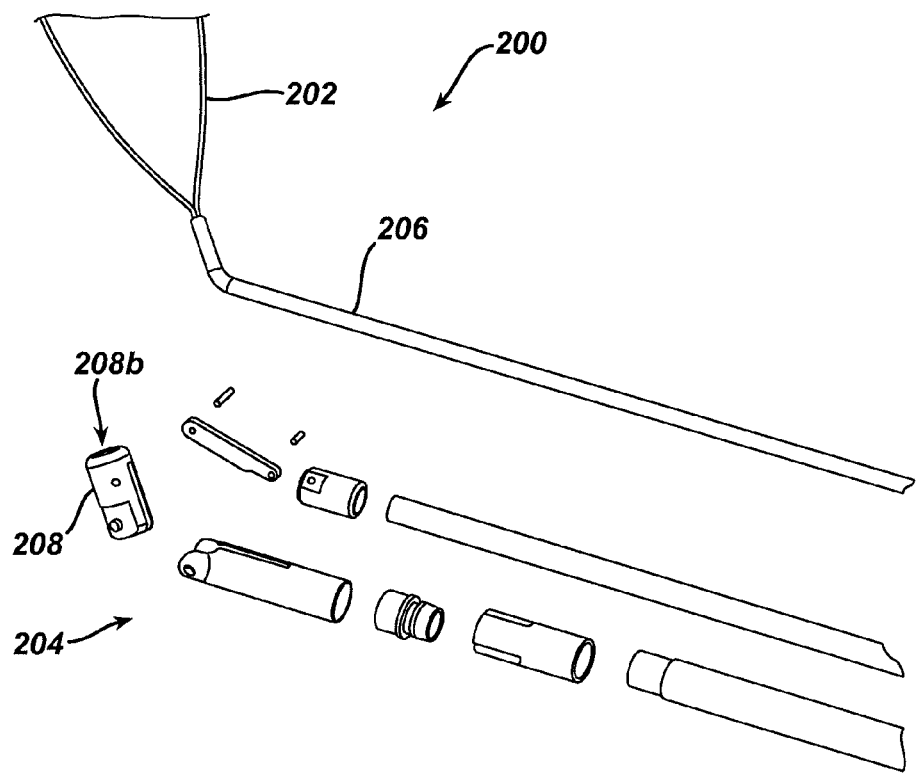
FIG. 5B is an exploded view of the insertion portion of FIG. 5A.

While devices discussed above are described and shown in connection with grasper jaws, a variety of other end effectors for performing various surgical procedures can be used. For example, as previously described with respect to FIGS. 2A and 2B, the end effector 14' can be in the form of biopsy forceps. Other jaw types can also be used including scissors and other cutting devices. The end effector can also include other features, such as a tissue-penetrating spike 41' formed between the jaws 18a', 18b', as further shown in FIGS. 2A-2B. The illustrated spike 41' can be used in combination with any type of end effector have opposed jaws, or with various other end effectors known in the art. FIGS. 5A and 5B illustrate another embodiment of an end effector in the form of a snare loop. As shown, the snare loop is formed from an elongate wire 200 that is folded such that a looped portion 202 of the wire 200 extends from a distal end $204_b$ of the insertion shaft 204 of the device. The trailing ends of the wire 200 can extend through the device and form the actuation wire, or they can be coupled to an actuation wire, as previously described. As further shown in FIG. 5B, the wire 200 can also be disposed within an insulating sheath 206 for insulating the device from any electrical energy delivered to the looped portion 202. The insulating sheath 206 can move in coordination with the wire 202, forming part of the actuation wire that is effective to actuate the end effector. The remaining components of the illustrated end effector are similar to those previously described with respect to FIGS. 1A-1D, except that the second link 208 can include a bore 208b formed in the distal end thereof for receiving the snare wire 200 and the insulating sheath 206 therethrough. In use, proximal movement of the snare wire 200 will pull the loop 202 proximally into the second link 208. As a result, the loop 202 will decrease in size, thus allowing the loop 202 to grasp and engage tissue to be removed. Conversely, distal movement of the snare wire 200 will push the loop 2002 distally beyond the second link 208, thereby increasing a size of the loop 202.

Figure 6:
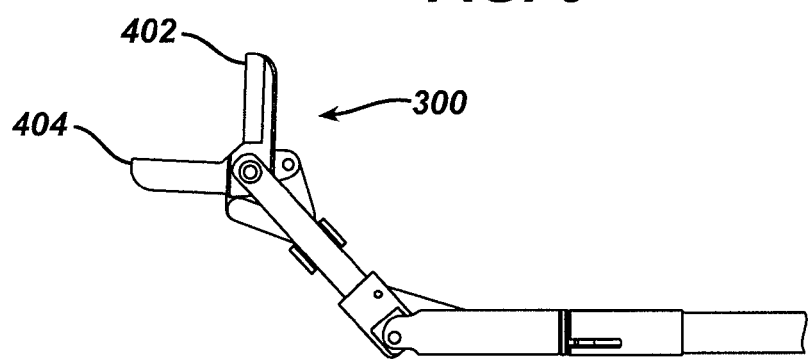
FIG. 6 is a perspective view of another embodiment of an end effector having scissors for use with a manually articulating device.
Figure 7:
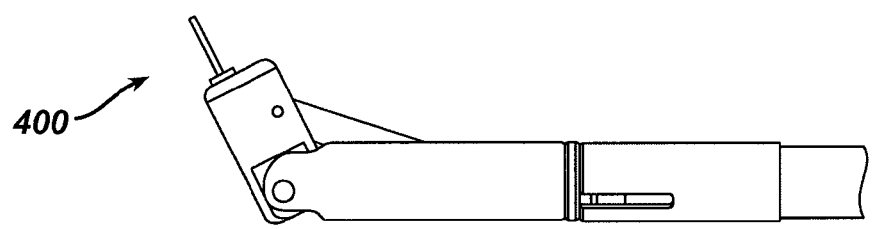
FIG. 7 is a perspective view of another embodiment of an end effector having a needle knife for use with a manually articulating device.
Figure 8:
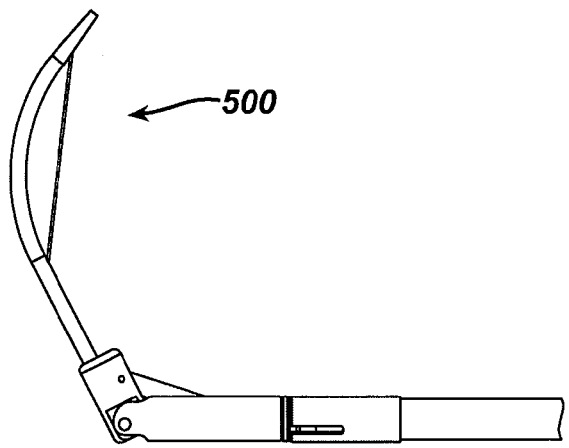
FIG. 8 is a perspective view of another embodiment of an end effector having a sphincterotome for use with a manually articulating device.

FIGS. 6-8 illustrate various other embodiments of end effectors that can be used with the manually articulating devices disclosed herein. In particular, FIG. 6 illustrates a pair of scissors 300, FIG. 7 illustrates a needle knife 400 (also referred to as a papillotome), and FIG. 8 illustrates a sphincterotome 500. The scissors 300 have a configuration similar to the biopsy jaws and forceps previously described herein, however each jaw 402, 404 has a blade-like configuration for cutting tissue. The needle knife 400 and sphincterotome 500 have a configuration similar to the snare loop, however the needle knife 400 is merely an elongate wire for cutting and/or coagulating tissue and the sphincterotome 500 has a bow-type configuration for cutting tissue. The needle knife 400 and sphincterotome 500 can also be configured to receive energy. A person skilled in the art will appreciate that a variety of other end effectors can be used other than those described and illustrated herein.

As indicated above, the various devices disclosed herein for controlling movement of a working end of a surgical device can be used in a variety of surgical procedures, including endoscopic procedures, laparoscopic procedures, and in conventional open surgical procedures, including robotic-assisted surgery. In one exemplary endoscopic procedure, an elongate shaft of a surgical device, such as one previously disclosed herein, can be inserted through a natural orifice and a body lumen to position an end effector located at a distal end of the elongate shaft adjacent to tissue to be treated. An articulation actuator can be translated along a longitudinal axis of the elongate shaft to cause a three-bar linkage to laterally articulate the end effector in a direction substantially perpendicular to a longitudinal axis of the elongate shaft to allow the end effector to be angularly oriented relative to the elongate shaft. This can be achieved by actuating one or more actuation mechanisms formed on a handle of the device. The method can also include rotating the end effector relative to the elongate shaft. In one embodiment, the three-bar linkage can rotate with the end effector relative to the elongate shaft. For example, the articulation actuator can be rotated relative to the elongate shaft to rotate both the three-bar linkage and the end effector. In another embodiment, the end effector can rotate relative to the three-bar linkage. For example, an actuation wire coupled to the end effector and extending through the elongate shaft and the three-bar linkage can be rotated. Once the end effector is positioned as desired, the end effector can be used to perform a surgical procedure.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   an elongate shaft having proximal and distal ends;
   a three-bar linkage having proximal and distal ends, the three-bar linkage including a first pivot joint, a second pivot joint, and a rotation joint, the rotation joint rotatably coupling the proximal end of the three-bar linkage to the distal end of the elongate shaft such that the three-bar linkage can rotate about a longitudinal axis of the elongate shaft;
   an end effector coupled to the distal end of the three-bar linkage; and
   an articulation actuator extending through the elongate shaft, the articulation actuator being coupled to the three-bar linkage at a third pivot joint and being effective to laterally articulate the three-bar linkage relative to a longitudinal axis of the elongate shaft to angularly orient the end effector relative to the elongate shaft, the articulation actuator having a distal end adjacent to the distal end of the elongate shaft,
   wherein the articulation actuator is rotatable about the longitudinal axis of the elongate shaft such that rotation of the articulation actuator about the longitudinal axis of the elongate shaft rotates the three-bar linkage and the end effector relative to the elongate shaft.

2. The device of claim 1, wherein the three-bar linkage comprises:
   a first articulating link having a proximal end coupled to the distal end of the elongate shaft at the rotation joint;

a second articulating link having a proximal end pivotally coupled to a distal end of the first articulating link at the first pivot joint, and a distal end coupled to the end effector; and a third articulating link having a proximal end pivotally coupled to the articulation actuator extending through the elongate shaft, and a distal end pivotally coupled to the second articulating link at the second pivot joint.

3. The device of claim 2, wherein the third articulating link comprises a flexible wire adapted to buckle when a force is applied thereto to cause the second articulating link to pivot relative to the first articulating link.

4. The device of claim 2, wherein the third articulating link comprises a cam having a cam slot formed therein for receiving a pin formed on the second articulating link such that movement of the cam is effective to cause the second articulating link to pivot relative to the first articulating link.

5. The device of claim 2, wherein the articulation actuator is adapted to translate along a longitudinal axis of the elongate shaft to laterally articulate the second link and the end effector relative to the first link.

6. The device of claim 2, wherein the articulation actuator comprises a hollow elongate tube.

7. The device of claim 1, wherein the end effector is selected from the group consisting of a grasper, a biopsy probe, a snare loop, forceps, scissors, a needle knife, and a sphincterotome.

8. The device of claim 1, further comprising an actuation wire extending through the elongate shaft and the three-bar linkage and adapted to translate along a longitudinal axis of the elongate shaft to actuate the end effector.

9. The device of claim 1, wherein the elongate shaft is flexible.

10. A method for processing the device of claim 1 for surgery, comprising:
a) obtaining the device of claim 1;
b) sterilizing the device; and
c) storing the device in a sterile container.

11. A manually articulating device, comprising:
an elongate shaft having proximal and distal ends;
a first link having a proximal end coupled to the distal end of the elongate shaft at a rotation joint;
a second link having a proximal end pivotally and directly coupled to a distal end of the first link;
an end effector directly coupled to a distal end of the second link;
a third link having a distal end pivotally and directly coupled to the second link; and
an articulation actuator extending through the elongate shaft and having a distal end directly coupled to a proximal end of the third link, the articulation actuator being adapted to translate along a longitudinal axis of the elongate shaft such that translation of the articulation actuator is adapted to laterally articulate the second link and the end effector relative to the first link and the elongate shaft, the articulation actuator having a distal end adjacent to the distal end of the elongate shaft, wherein the first link is rotatably coupled to the elongate shaft such that the first link, second link, third link, and end effector are rotatable about a longitudinal axis of the elongate shaft and wherein the articulation actuator is rotatable about the longitudinal axis of the elongate shaft such that rotation of the articulation actuator about the longitudinal axis of the elongate shaft is effective to rotate the first link, second link, third link, and end effector relative to the elongate shaft.

12. The device of claim 11, wherein the third link comprises a flexible wire adapted to buckle when a force is applied thereto to cause the second link to pivot relative to the first link.

13. The device of claim 11, wherein the third link comprises a cam having a cam slot formed therein for receiving a pin formed on the second link such that movement of the cam is effective to cause the second link to pivot relative to the first link.

14. The device of claim 11, wherein the articulation actuator comprises a hollow elongate tube.

15. The device of claim 11, wherein the end effector is rotatably coupled to the second link.

16. The device of claim 11, wherein proximal movement of the articulation actuator is adapted to laterally articulate the second link and the end effector in a first lateral direction, and distal movement of the articulation actuator is adapted to longitudinally align the second link and the end effector with the longitudinal axis of the elongate shaft.

17. The device of claim 11, wherein proximal movement of the articulation actuator is effective to move the third link proximally, which causes the second link to pivot relative to the first link.

18. The device of claim 11, wherein the end effector is selected from the group consisting of a grasper, a biopsy probe, a snare loop, forceps, scissors, a needle knife, and a sphincterotome.

19. The device of claim 11, wherein the elongate shaft is flexible.

20. The device of claim 1, wherein the end effector is coupled to the distal end of the three-bar linkage at a pivot joint located distal to the first and second pivot joints and the rotation joint.

21. The device of claim 2, wherein the rotation joint of the three-bar linkage comprises a first rotation coupling having a proximal end fixedly mated to the elongate shaft and a second rotation coupling having a distal end fixedly mated to the first link, the first and second rotation couplings being rotatably mated to one another.

22. The device of claim 1, wherein the elongate shaft includes a first rotation coupling fixedly mated to a distal end thereof.

23. The device of claim 22, wherein the three-bar linkage include a second rotation coupling fixedly mated to a proximal end thereof, and wherein the second rotation coupling is rotatably mated to the first rotation coupling at the rotation joint.

* * * * *